US010076384B2

(12) United States Patent
Kasprzyk et al.

(10) Patent No.: US 10,076,384 B2
(45) Date of Patent: Sep. 18, 2018

(54) BALLOON CATHETER APPARATUS WITH MICROWAVE EMITTER

(71) Applicant: SYMPLE SURGICAL INC., Flagstaff, AZ (US)

(72) Inventors: Daniel Kasprzyk, Flagstaff, AZ (US); Justin Preston, San Francisco, CA (US); Seth Crozier, Dublin, CA (US); Sohail Desai, Mountain View, CA (US); Roger D Watkins, Dunlap, IL (US); Balamurugan Sundaram, Dunlap, IL (US); Sureshbabu Sundaram, Dunlap, IL (US)

(73) Assignee: Symple Surgical, Inc., Flagstaff, AZ (US)

( * ) Notice: Subject to any disclaimer, the term of this patent is extended or adjusted under 35 U.S.C. 154(b) by 681 days.

(21) Appl. No.: 14/483,148

(22) Filed: Sep. 10, 2014

(65) Prior Publication Data

US 2015/0080875 A1 Mar. 19, 2015

Related U.S. Application Data

(63) Continuation-in-part of application No. 14/199,374, filed on Mar. 6, 2014.
(Continued)

(51) Int. Cl.
*A61B 18/18* (2006.01)
*A61B 18/00* (2006.01)

(52) U.S. Cl.
CPC ...... *A61B 18/1815* (2013.01); *A61B 2018/00023* (2013.01); *A61B 2018/00285* (2013.01);
(Continued)

(58) Field of Classification Search
CPC ...... A61B 18/1815; A61B 2018/00023; A61B 2018/00285; A61B 2018/00351;
(Continued)

(56) References Cited

U.S. PATENT DOCUMENTS 4,554,929 A 11/1985 Samson et al.
4,643,186 A 2/1987 Rosen et al.
(Continued)

FOREIGN PATENT DOCUMENTS

AU 8295998 A 2/1999
AU 3863100 A 9/2000
(Continued)

OTHER PUBLICATIONS

Extended European Search Report for European Patent Application No. 14760518.2 dated Nov. 8, 2016 (6 pages).
(Continued)

*Primary Examiner* — Michael Peffley
*Assistant Examiner* — Amanda Zink
(74) *Attorney, Agent, or Firm* — Skinner and Associate; Joel Skinner

(57) ABSTRACT

A microwave ablation system and method is disclosed comprising a balloon catheter apparatus and a control system. The balloon catheter apparatus comprises a catheter configured to house a coaxial cable and one or more coolant channels, an inflatable balloon located at the distal end of the catheter, and an antenna positioned in the inflatable balloon and in communication with the coaxial cable. The control system comprises a fluid pump configured to introduce fluid into a proximal end of the catheter, a power amplifier capable of generating microwave energy for delivery to the target tissue zone for at least one energy application cycle ranging from 60 seconds to 600 seconds at a frequency ranging from 2.4 GHz to 2.5 GHz, and a computer system configured to monitor and/or regulate the delivery of microwave energy to the target tissue, the fluid pump, at least one sensor, and antenna reflected power.

18 Claims, 19 Drawing Sheets

Related U.S. Application Data

(60) Provisional application No. 61/775,281, filed on Mar. 8, 2013.

(52) U.S. Cl.
CPC ............ *A61B 2018/00351* (2013.01); *A61B 2018/00404* (2013.01); *A61B 2018/00577* (2013.01); *A61B 2018/00642* (2013.01); *A61B 2018/00714* (2013.01); *A61B 2018/183* (2013.01); *A61B 2018/1861* (2013.01); *A61B 2018/1884* (2013.01)

(58) Field of Classification Search
CPC ........... A61B 2018/00404; A61B 2018/00577; A61B 2018/00642; A61B 2018/00714; A61B 2018/183; A61B 2018/1861; A61B 2018/1884
See application file for complete search history.

(56) References Cited

U.S. PATENT DOCUMENTS

| | | | |
|---|---|---|---|
| 4,808,164 A | 2/1989 | Hess et al. | |
| 4,924,863 A | 5/1990 | Sterzer et al. | |
| 4,927,413 A | 5/1990 | Hess et al. | |
| 4,967,765 A | 11/1990 | Turner et al. | |
| 5,057,106 A | 10/1991 | Kasevich et al. | |
| 5,061,267 A | 10/1991 | Zeiher et al. | |
| 5,114,423 A | 5/1992 | Kasprzyk et al. | |
| 5,129,396 A | 7/1992 | Rosen et al. | |
| 5,232,441 A | 8/1993 | Stephen et al. | |
| 5,275,597 A | 1/1994 | Higgins et al. | |
| 5,295,959 A | 3/1994 | Gurbel et al. | |
| 5,334,193 A | 8/1994 | Nardella | |
| 5,386,837 A | 2/1995 | Sterzer | |
| 5,417,689 A | 5/1995 | Fine et al. | |
| 5,462,521 A | 10/1995 | Brucker et al. | |
| 5,470,352 A | 11/1995 | Rappaport et al. | |
| 5,496,271 A | 3/1996 | Burton et al. | |
| 5,571,147 A | 11/1996 | Sluijter et al. | |
| 5,746,701 A | 5/1998 | Noone | |
| 5,766,605 A | 6/1998 | Sanders et al. | |
| 5,776,176 A | 7/1998 | Rudie | |
| 5,800,486 A | 9/1998 | Thome et al. | |
| 5,810,804 A | 9/1998 | Gough et al. | |
| 5,853,408 A | 12/1998 | Muni et al. | |
| 5,861,021 A | 1/1999 | Thome et al. | |
| 5,899,899 A | 5/1999 | Arless et al. | |
| 5,967,988 A | 10/1999 | Briscoe et al. | |
| 5,987,360 A | 11/1999 | McGrath et al. | |
| 5,992,419 A | 11/1999 | Sterzer et al. | |
| 6,001,856 A | 12/1999 | Dow et al. | |
| 6,004,269 A | 12/1999 | Crowley et al. | |
| 6,096,068 A | 8/2000 | Dobak et al. | |
| 6,097,985 A | 8/2000 | Kasevich et al. | |
| 6,181,970 B1 | 1/2001 | Kasevich | |
| 6,184,254 B1 | 2/2001 | Bukoski et al. | |
| 6,217,576 B1 | 4/2001 | Tu et al. | |
| 6,223,085 B1 | 4/2001 | Dann et al. | |
| 6,224,624 B1 | 5/2001 | Lasheras et al. | |
| 6,226,553 B1 | 5/2001 | Carl et al. | |
| 6,230,060 B1 | 5/2001 | Mawhinney | |
| 6,233,490 B1 | 5/2001 | Kasevich | |
| 6,235,019 B1 | 5/2001 | Lehmann et al. | |
| 6,251,130 B1 | 6/2001 | Dobak, III et al. | |
| 6,290,715 B1 | 9/2001 | Sharkey et al. | |
| 6,292,695 B1 | 9/2001 | Webster, Jr. et al. | |
| 6,312,452 B1 | 11/2001 | Dobak, III et al. | |
| 6,411,852 B1 | 6/2002 | Danek et al. | |
| 6,419,653 B2 | 7/2002 | Edwards et al. | |
| 6,450,988 B1 | 9/2002 | Bradshaw | |
| 6,464,626 B1 | 10/2002 | Peterson | |
| 6,491,716 B2 | 12/2002 | Dobak, III et al. | |
| 6,496,737 B2 | 12/2002 | Rudie et al. | |
| 6,506,189 B1 | 1/2003 | Rittman, III et al. | |
| 6,540,740 B2 | 4/2003 | Lehmann et al. | |
| 6,551,349 B2 | 4/2003 | Lasheras et al. | |
| 6,575,933 B1 | 6/2003 | Wittenberger et al. | |
| 6,582,417 B1 | 6/2003 | Ledesma et al. | |
| 6,602,247 B2 | 8/2003 | Lalonde | |
| 6,605,031 B1 | 8/2003 | Mourtada et al. | |
| 6,623,515 B2 | 9/2003 | Mulier et al. | |
| 6,656,216 B1 | 12/2003 | Hossainy et al. | |
| 6,669,689 B2 | 12/2003 | Lehmann et al. | |
| 6,669,691 B1 | 12/2003 | Taimisto | |
| 6,692,481 B2 | 2/2004 | Guerrero | |
| 6,699,241 B2 | 3/2004 | Rappaport et al. | |
| 6,702,811 B2 | 3/2004 | Stewart et al. | |
| 6,719,723 B2 | 4/2004 | Werneth | |
| 6,726,684 B1 | 4/2004 | Woloszko et al. | |
| 6,733,435 B2 | 5/2004 | Canedo | |
| 6,736,835 B2 | 5/2004 | Pellegrino et al. | |
| 6,752,802 B1 * | 6/2004 | Isenberg ................ | A61B 18/04 606/28 |
| 6,814,712 B1 | 11/2004 | Edwards et al. | |
| 6,827,716 B2 | 12/2004 | Ryan et al. | |
| 6,847,848 B2 | 1/2005 | Sterzer | |
| 6,896,886 B2 | 5/2005 | Aoki et al. | |
| 6,899,709 B2 | 5/2005 | Lehmann et al. | |
| 6,907,884 B2 | 6/2005 | Pellegrino et al. | |
| 6,913,604 B2 | 7/2005 | Mihalik et al. | |
| 6,929,632 B2 | 8/2005 | Nita et al. | |
| 6,942,659 B2 | 9/2005 | Lehmann et al. | |
| 6,952,615 B2 | 10/2005 | Satake | |
| 6,953,469 B2 | 10/2005 | Ryan | |
| 6,977,080 B1 | 12/2005 | Donovan | |
| 6,978,174 B2 | 12/2005 | Gelfand et al. | |
| 7,018,399 B2 | 3/2006 | Dobak, III et al. | |
| 7,063,696 B2 | 6/2006 | Taimisto | |
| 7,089,063 B2 | 8/2006 | Lesh et al. | |
| 7,090,635 B2 | 8/2006 | Ledesma et al. | |
| 7,156,843 B2 | 1/2007 | Skarda | |
| 7,162,303 B2 | 1/2007 | Levin et al. | |
| 7,163,504 B1 | 1/2007 | Chiu et al. | |
| 7,217,282 B2 | 5/2007 | Ginsburg et al. | |
| 7,247,269 B2 | 7/2007 | Keidar | |
| 7,294,142 B2 | 11/2007 | Dobak, III et al. | |
| 7,300,433 B2 | 11/2007 | Lane et al. | |
| 7,322,973 B2 | 1/2008 | Nahon | |
| 7,331,956 B2 | 2/2008 | Hovda et al. | |
| 7,340,307 B2 | 3/2008 | Maguire et al. | |
| 7,351,254 B2 | 4/2008 | Magers | |
| 7,357,799 B2 | 4/2008 | Ryan et al. | |
| 7,395,119 B2 | 7/2008 | Hagen et al. | |
| 7,410,486 B2 | 8/2008 | Fuimaono et al. | |
| 7,422,600 B2 | 9/2008 | Dobak, III | |
| 7,462,178 B2 | 12/2008 | Woloszko et al. | |
| 7,476,234 B2 | 1/2009 | Evans et al. | |
| 7,485,624 B2 | 2/2009 | Donovan | |
| 7,494,661 B2 | 2/2009 | Sanders | |
| 7,499,747 B2 | 3/2009 | Kieval et al. | |
| 7,591,814 B2 | 9/2009 | Santoianni et al. | |
| 7,593,778 B2 | 9/2009 | Chandran et al. | |
| 7,594,900 B1 | 9/2009 | Nash et al. | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,753,905 B2 | 7/2010 | Lehmann et al. | |
| 7,756,583 B2 | 7/2010 | Demarais et al. | |
| 7,758,571 B2 | 7/2010 | Saadat | |
| 7,766,871 B2 | 8/2010 | Hirszowicz et al. | |
| 7,776,034 B2 | 8/2010 | Kampa | |
| 7,794,454 B2 | 9/2010 | Abboud et al. | |
| 7,799,021 B2 | 9/2010 | Leung et al. | |
| 7,819,826 B2 | 10/2010 | Diederich et al. | |
| 7,819,862 B2 | 10/2010 | Pachon Mateos et al. | |
| 7,842,012 B2 | 11/2010 | Ellis et al. | |
| 7,853,333 B2 | 12/2010 | Demarais | |
| 7,873,417 B2 | 1/2011 | Demarais et al. | |
| 7,914,526 B2 | 3/2011 | Lehmann et al. | |
| 7,937,143 B2 | 5/2011 | Demarais et al. | |

(56) References Cited

U.S. PATENT DOCUMENTS

| | | |
|---|---|---|
| 7,945,331 B2 | 5/2011 | Vilims |
| 7,949,400 B2 | 5/2011 | Kieval et al. |
| 7,998,182 B2 | 8/2011 | Dobak, III et al. |
| 8,010,195 B2 | 8/2011 | Sunagawa et al. |
| 8,010,199 B2 | 8/2011 | Sunagawa et al. |
| 8,038,675 B2 | 10/2011 | Pachon Mateos et al. |
| 8,043,284 B2 | 10/2011 | Lehmann et al. |
| 8,105,262 B2 | 1/2012 | Noda et al. |
| 8,116,873 B2 | 2/2012 | Anderson et al. |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,759 B2 | 4/2012 | Atanasoska et al. |
| 8,175,711 B2 | 5/2012 | Demarais et al. |
| 8,241,272 B2 | 8/2012 | Arnold et al. |
| 8,347,891 B2 | 1/2013 | Demarais et al. |
| 8,433,423 B2 | 4/2013 | Demarais |
| 8,444,640 B2 | 5/2013 | Demarais et al. |
| 8,460,285 B2 | 6/2013 | Wang et al. |
| 8,545,491 B2 | 10/2013 | Abboud et al. |
| 8,679,106 B2 | 3/2014 | Ormsby et al. |
| 8,728,073 B2 | 5/2014 | McDaniel |
| 9,333,035 B2 | 5/2016 | Rudie |
| 2002/0068897 A1 | 6/2002 | Jenkins et al. |
| 2003/0040782 A1 | 2/2003 | Walker et al. |
| 2003/0060813 A1 | 3/2003 | Loeb et al. |
| 2003/0065317 A1 | 4/2003 | Rudie et al. |
| 2003/0195496 A1 | 10/2003 | Maquire et al. |
| 2003/0195510 A1 | 10/2003 | Schaer |
| 2003/0199914 A1 | 10/2003 | Diaz |
| 2004/0019364 A1 | 1/2004 | Kieval et al. |
| 2004/0047807 A1 | 3/2004 | Meyer |
| 2005/0065504 A1 | 3/2005 | Melsky et al. |
| 2005/0137667 A1 | 6/2005 | Omar-Pasha et al. |
| 2005/0165391 A1 | 7/2005 | Maguire et al. |
| 2005/0228370 A1 | 10/2005 | Sterzer et al. |
| 2005/0261672 A1 | 11/2005 | Deem et al. |
| 2006/0004417 A1 | 1/2006 | Rossing et al. |
| 2006/0041277 A1 | 2/2006 | Deem et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0216279 A1 | 9/2006 | Glass et al. |
| 2006/0265038 A1 | 11/2006 | Hagen et al. |
| 2006/0271111 A1 | 11/2006 | Demarais et al. |
| 2006/0276852 A1 | 12/2006 | Demarais et al. |
| 2006/0293712 A1 | 12/2006 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0060972 A1 | 3/2007 | Kieval et al. |
| 2007/0083239 A1 | 4/2007 | Demarais et al. |
| 2007/0129760 A1 | 6/2007 | Demarais et al. |
| 2007/0156198 A1 | 7/2007 | Rossing et al. |
| 2007/0167984 A1 | 7/2007 | Kieval et al. |
| 2007/0185554 A1 | 8/2007 | Appling et al. |
| 2007/0219548 A1 | 9/2007 | Carr |
| 2007/0265687 A1 | 11/2007 | Deem et al. |
| 2007/0276442 A1 | 11/2007 | Hagen et al. |
| 2008/0015570 A1 | 1/2008 | Ormsby et al. |
| 2008/0027505 A1 | 1/2008 | Levin et al. |
| 2008/0097422 A1 | 4/2008 | Edwards |
| 2008/0103573 A1 | 5/2008 | Gerber |
| 2008/0139641 A1 | 6/2008 | Meyer |
| 2008/0140167 A1 | 6/2008 | Hagen et al. |
| 2008/0167699 A1 | 7/2008 | Kieval et al. |
| 2008/0172104 A1 | 7/2008 | Kieval et al. |
| 2008/0177349 A1 | 7/2008 | Kieval et al. |
| 2008/0177350 A1 | 7/2008 | Kieval et al. |
| 2008/0215111 A1 | 9/2008 | Kieval et al. |
| 2008/0234779 A1 | 9/2008 | Pedersen et al. |
| 2008/0288017 A1 | 11/2008 | Kieval et al. |
| 2009/0030262 A1 | 1/2009 | Kieval et al. |
| 2009/0216284 A1 | 8/2009 | Chin et al. |
| 2010/0010567 A1 | 1/2010 | Deem et al. |
| 2010/0049178 A1 | 2/2010 | Deem et al. |
| 2010/0057072 A1 | 3/2010 | Roman et al. |
| 2010/0137952 A1 | 6/2010 | Demarais et al. |
| 2010/0145331 A1 | 6/2010 | Chrisitian et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0286684 A1 | 11/2010 | Hata et al. |
| 2010/0312096 A1 | 12/2010 | Guttman et al. |
| 2011/0077633 A1* | 3/2011 | Bonn ............ A61B 18/1815 606/33 |
| 2011/0104060 A1 | 5/2011 | Seward |
| 2011/0104061 A1 | 5/2011 | Seward |
| 2011/0112400 A1 | 5/2011 | Emery et al. |
| 2011/0118725 A1 | 5/2011 | Mayse et al. |
| 2011/0137149 A1 | 6/2011 | Gertner |
| 2011/0137298 A1 | 6/2011 | Nguyen et al. |
| 2011/0137365 A1 | 6/2011 | Ben-Ezra et al. |
| 2011/0160723 A1 | 6/2011 | Tullis et al. |
| 2011/0166499 A1 | 7/2011 | Demarais et al. |
| 2011/0184337 A1 | 7/2011 | Evans et al. |
| 2011/0207758 A1 | 8/2011 | Sobotka et al. |
| 2011/0208175 A1 | 8/2011 | Sobotka et al. |
| 2011/0224749 A1 | 9/2011 | Ben-David et al. |
| 2011/0257523 A1 | 10/2011 | Hastings et al. |
| 2011/0257524 A1 | 10/2011 | Gertner |
| 2011/0257564 A1 | 10/2011 | Demarais et al. |
| 2011/0257641 A1 | 10/2011 | Hastings et al. |
| 2011/0264089 A1 | 10/2011 | Zirkle et al. |
| 2011/0270246 A1 | 11/2011 | Clark et al. |
| 2011/0306851 A1 | 12/2011 | Wang |
| 2011/0307034 A1 | 12/2011 | Hastings et al. |
| 2012/0016358 A1 | 1/2012 | Mayse et al. |
| 2012/0029420 A1 | 2/2012 | Rittman, III et al. |
| 2012/0065493 A1 | 3/2012 | Gertner |
| 2012/0065554 A1 | 3/2012 | Pikus |
| 2012/0095335 A1 | 4/2012 | Sverdlik et al. |
| 2012/0095371 A1 | 4/2012 | Sverdlik et al. |
| 2012/0095461 A1 | 4/2012 | Herscher et al. |
| 2012/0108517 A1 | 5/2012 | Evans et al. |
| 2012/0109021 A1 | 5/2012 | Hastings et al. |
| 2012/0116486 A1* | 5/2012 | Naga ............ A61B 18/1815 607/102 |
| 2012/0130368 A1 | 5/2012 | Jenson |
| 2012/0157988 A1* | 6/2012 | Stone ............ A61B 5/02007 606/33 |
| 2013/0072928 A1 | 3/2013 | Schaer |
| 2013/0231521 A1 | 9/2013 | Farnan |
| 2014/0021197 A1* | 1/2014 | Brannan ............ A61B 18/18 219/705 |
| 2014/0046174 A1 | 2/2014 | Ladtkow et al. |
| 2014/0046315 A1 | 2/2014 | Ladtkow et al. |
| 2014/0081254 A1* | 3/2014 | Rudie ............ A61B 18/1815 606/27 |
| 2014/0214018 A1 | 7/2014 | Behar |
| 2015/0119870 A1 | 4/2015 | Rudie |

FOREIGN PATENT DOCUMENTS

| | | |
|---|---|---|
| CA | 2057924 | 11/1990 |
| CA | 2737785 | 3/2010 |
| CN | 102198015 | 9/2011 |
| CN | 202761434 U | 3/2013 |
| EP | 344279 | 3/1992 |
| EP | 474734 | 3/1992 |
| EP | 797956 | 6/2003 |
| EP | 579599 | 1/2005 |
| EP | 1534159 | 6/2005 |
| EP | 1802370 A2 | 7/2007 |
| EP | 1870031 | 12/2007 |
| EP | 1802370 B1 | 1/2011 |
| EP | 2329859 | 6/2011 |
| JP | H06191 A | 1/1994 |

(56) References Cited

FOREIGN PATENT DOCUMENTS

| | | |
|---|---|---|
| JP | 6233823 | 8/1994 |
| JP | H07308382 A | 11/1995 |
| JP | H08187298 A | 7/1996 |
| JP | 2002011101 | 1/2002 |
| WO | WO 1992011850 | 7/1992 |
| WO | WO 9400178 | 1/1994 |
| WO | WO 9402204 | 2/1994 |
| WO | WO 1994009808 | 5/1994 |
| WO | WO 9426188 | 11/1994 |
| WO | WO 9600041 | 1/1996 |
| WO | WO 9640347 | 12/1996 |
| WO | WO 9741924 | 11/1997 |
| WO | WO 1997042951 | 11/1997 |
| WO | WO 1998017190 | 4/1998 |
| WO | WO 2000062699 | 10/2000 |
| WO | WO 2001015770 | 3/2001 |
| WO | WO 2001043528 | 6/2001 |
| WO | WO 2001089619 | 11/2001 |
| WO | WO 2002011636 | 2/2002 |
| WO | WO 2002024248 | 3/2002 |
| WO | WO 2002047577 | 6/2002 |
| WO | WO 2002094842 | 11/2002 |
| WO | WO 2003018821 | 3/2003 |
| WO | WO 2003082403 | 10/2003 |
| WO | WO 2005009219 | 2/2005 |
| WO | WO 2005032637 | 4/2005 |
| WO | WO 2005084389 | 9/2005 |
| WO | WO 2005105827 | 11/2005 |
| WO | WO 2006041847 | 4/2006 |
| WO | WO 2006041881 | 4/2006 |
| WO | WO 2006063154 | 6/2006 |
| WO | WO 2006074390 | 7/2006 |
| WO | WO 2006099285 | 9/2006 |
| WO | WO 2006121558 | 11/2006 |
| WO | WO 2006125163 | 11/2006 |
| WO | WO 2007025198 | 3/2007 |
| WO | WO 2007044874 | 4/2007 |
| WO | WO 2007103879 | 9/2007 |
| WO | WO 2007103881 | 9/2007 |
| WO | WO 2007121309 | 10/2007 |
| WO | WO 2007124169 | 11/2007 |
| WO | WO 2008016924 | 2/2008 |
| WO | WO 2008047243 | 4/2008 |
| WO | WO 2008061150 | 5/2008 |
| WO | WO 2008070413 | 6/2008 |
| WO | WO 2008131302 | 10/2008 |
| WO | WO 2008131306 | 10/2008 |
| WO | WO 2009018492 | 2/2009 |
| WO | WO 2009086536 | 7/2009 |
| WO | WO 2009137819 | 11/2009 |
| WO | WO 2010060100 | 5/2010 |
| WO | WO 2010067360 | 6/2010 |
| WO | WO 2010078175 | 7/2010 |
| WO | WO 2011053757 | 5/2011 |
| WO | WO 2011053772 | 5/2011 |
| WO | WO 2011056684 | 5/2011 |
| WO | WO 2011060200 | 5/2011 |
| WO | WO 2011060201 | 5/2011 |
| WO | WO 2011060339 | 5/2011 |
| WO | WO 2011075328 | 6/2011 |
| WO | WO 2011091069 | 7/2011 |
| WO | WO 2011094367 | 8/2011 |
| WO | WO 2011127216 | 10/2011 |
| WO | WO 2011130531 | 10/2011 |
| WO | WO 2011130534 | 10/2011 |
| WO | WO 2011139589 | 11/2011 |
| WO | WO 2012027641 | 3/2012 |
| WO | WO 2012033860 | 3/2012 |
| WO | WO 2012054762 | 4/2012 |
| WO | WO 2012058434 | 5/2012 |
| WO | WO 2012061150 | 5/2012 |
| WO | WO 2012061161 | 5/2012 |
| WO | 2013030806 A1 | 3/2013 |

OTHER PUBLICATIONS

International Search Report and Written Opinion for PCT/US2015/047954 dated Nov. 24, 2015.

Smithwick, R.H., et al., "Splanchnicectomy for essential hypertension," The Journal of the American Medical Association, vol. 152, No. 16, Aug. 15, 1953, pp. 1501-1504. (4 pages).

Schlaich, M. P., et al., "Renal denervation as a therapeutic approach for hypertension: Novel implications for an old concept," Hypertension: Journal of the American Heart Association, 2009, 54, pp. 1195-1201. (8 pages).

Bertog, S.C., et al., "Renal denervation for hypertension," JACC: Cardiovascular Interventions, Mar. 31, 2012, vol. 5, No. 3, pp. 249-258. (10 pages).

Esler, M.D., et al., "Renal sympathetic denervation in patients with treatment-resistant hypertension (The Symplicity HTN-2 Trial): a randomised controlled trial." Lancet, Dec. 4, 2010, 376 (9756): pp. 1878-1880. (Abstract only). (1 page).

Vitiello, V., et al., "Emerging Robotic Platforms for Minimally Invasive Surgery," IEEE Reviews in Biomedical Engineering, vol. 6, 2013, pp. 111-126 (16 pages).

Bertram, J. M., et al., "A Review of Coaxial-Based Interstitial Antennas for Hepatic Microwave Ablation," begell house, inc., Critical Reviews in Biomedical Engineering 34.3 (2006), pp. 187-213 (31 pages).

Wlodarczyk, W., et al., "Whole Body Hyperthermia Applicator Inside MR System: Simulations of Influence of RF Shield of MR Scanner on the Performance of Hyperthermia Applicator," Strahlenklinik und Poliklinik, Virchow-Klinikum, Humboldt-Universitiat zu Berlin, Technische Universitat Berlin, Germany (1996) (1 page).

Qiu, B., et al., "Development of an Intravascular Heating Source Using an MR Imaging Guidewire," Journal of Magnetic Resonance Imaging 16.6 (2002), pp. 716-720 (5 pages).

International Search Report and Written Opinion dated Jun. 25, 2014 for PCT Application No. PCT/US2014/021233 (14 pages).

International Preliminary Report on Patentability for PCT Application No. PCT/US2014/021233 dated Sep. 17, 2015 (8 pages).

\* cited by examiner

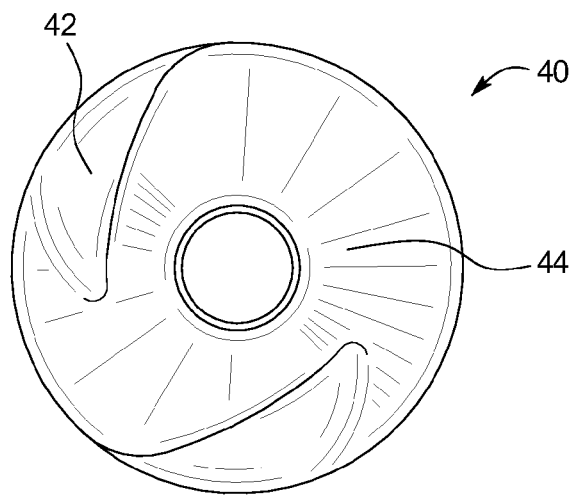
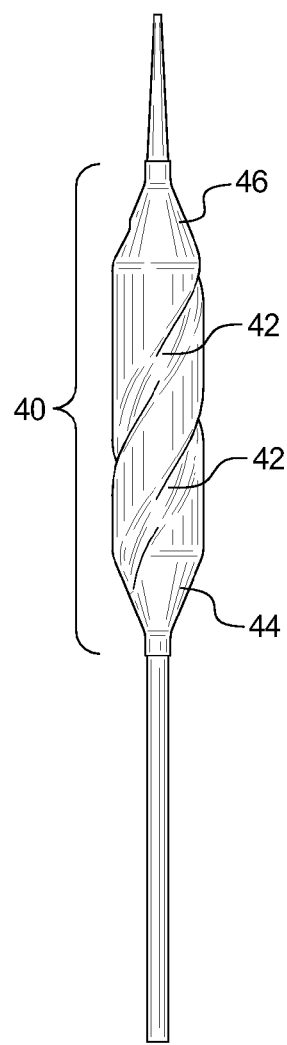

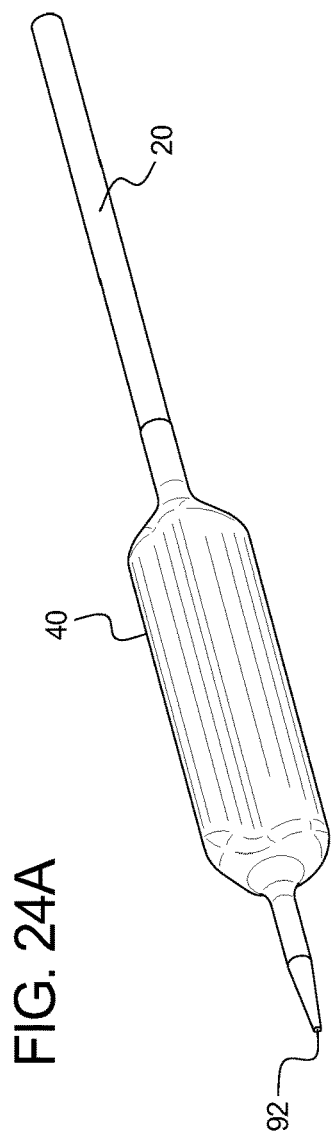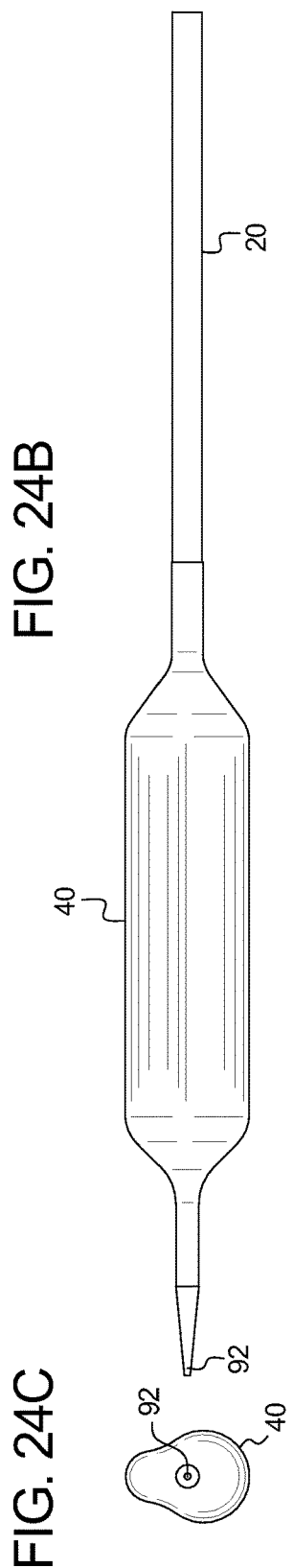
FIG. 24A
FIG. 24B
FIG. 24C

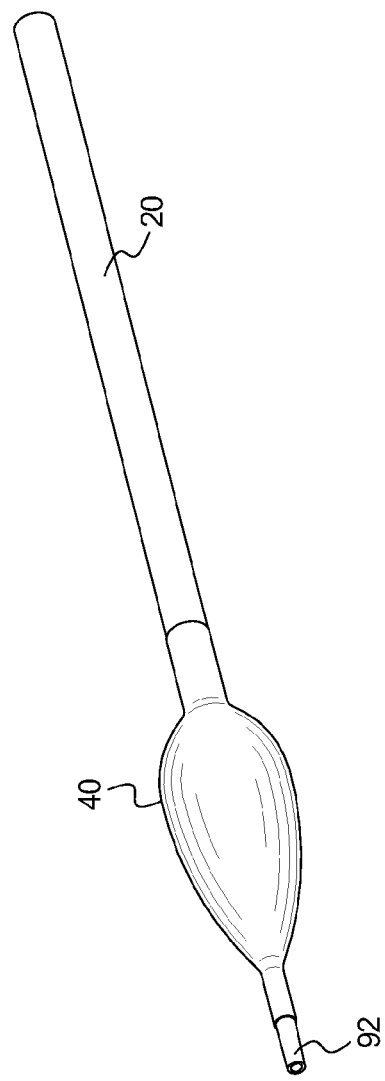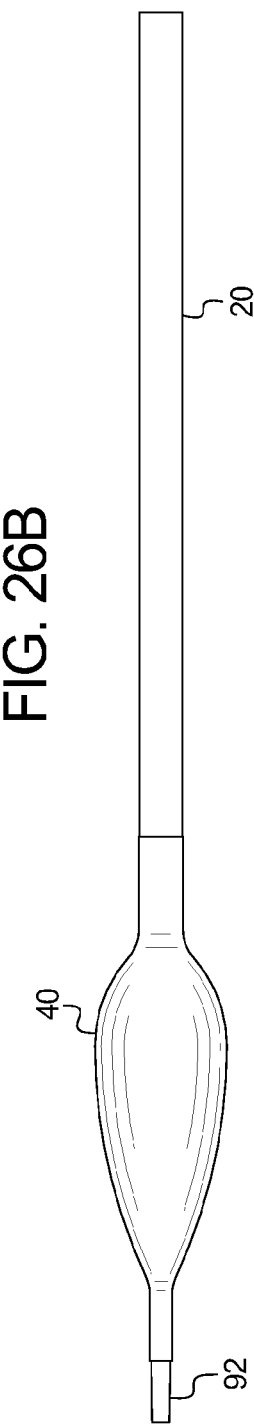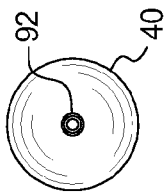
FIG. 26A
FIG. 26B
FIG. 26C

BALLOON CATHETER APPARATUS WITH MICROWAVE EMITTER

PRIORITY

This application is a continuation-in-part of U.S. patent application Ser. No. 14/199,374, which was filed on Mar. 6, 2014 and claims the benefit of U.S. Provisional Application No. 61/775,281, filed Mar. 8, 2013, which are hereby incorporated by reference in their entirety.

BACKGROUND

This application relates generally to balloon catheters, and more specifically to balloon catheter apparatuses and associated systems configured to emit electromagnetic waves in the form of microwave energy for treating disease.

Ablation catheters are well known in the art. The addition of a balloon to stabilize and secure the ablation catheter in a vessel has also been described. Ablation catheters are used in various medical procedures. Those skilled in the art will appreciate that ablation catheters can be used to treat atrial fibrillation, similar to the techniques described in U.S. Pat. No. 5,861,021, which is hereby incorporated by reference. Further, those skilled in the art can appreciate a balloon-stabilized thermal ablation catheter may be configured to be advanced through the vasculature to damage nerves associated with the nervous system thereby modulating the transmission of signals via the damaged nerves.

Specifically, balloon catheters containing a thermal energy emitter can be advanced via the vasculature and damage adjacent tissue on a cellular level, which in turn would modulate the transmission of certain signals originating from or carried through those damaged nerves. Renal sympathetic nerve activity is determined primarily by cardiovascular baroreceptors. Thus, decreases in perfusion pressure at the carotid sinus/aortic arch baroreceptors may reflexively raise renal sympathetic nerve activity and result in renal sympathetic nerve-dependent sodium retention. Conversely, volume expansion or mechanical stimulation of the atria results in a suppression of renal sympathetic nerve activity and a concomitant renal sympathetic nerve-mediated diuresis and natriuresis. Employing ablation balloon catheters to disrupt renal sympathetic nerve activity can thus treat cardiovascular and renal diseases where sympathetic nerve activity has negative physiologic consequences (e.g., hypertension, edema, congestive heart failure, etc.).

Conventional renal denervation techniques for treating cardiovascular hypertension involve one or more of a number of interventional methods to disrupt the renal sympathetic nerves. Examples of such techniques include thermal ablation, chemical ablation, and mechanical cutting devices incorporated in balloon catheters. However, the majority of the interventions are advanced through the vasculature to the renal artery, and because the renal artery is highly sensitive to thermal damage, use of such techniques may pose significant safety risks to the patient. One known risk associated with use of ablation catheters is that an energy emitter or probe with an elevated temperature may come into contact with the wall of the renal artery. If such an energy emitter or probe comes into contact with the renal artery wall, then the artery wall could be damaged and the lumen of the renal artery could narrow as a result of scarring and stenosis. Contact with a heated energy source or probe can cause unwanted tissue damage in other procedures outside renal denervation procedures, including cardiac tamponade, transient ischemic attacks, stroke, and death. Thus, known balloon catheter apparatuses have been ineffective at ablating targeted tissue while minimizing damage to healthy or untargeted tissue, or otherwise continue to pose safety risks to the patient.

Conventional balloon catheter systems that generate thermal energy using radio frequencies ("RF") rely on conduction of the heat from monopolar electrodes embedded in or near a surface of the balloon wall to the inner surface of the artery. The frequencies that are used in these systems to generate thermal energy are selected according to the conductive characteristics of the vessel and surrounding tissue. Moreover, such systems require the use of a return electrode to provide a return path for the electrical current. Because high frequency current travels through the body from the balloon to the return electrode, sensory nerve damage can occur and would result in patient pain due to heating at the interface between the skin and the electrode. A need exists for a balloon catheter system that capable of more precise energy delivery to minimize any sensory nerve damage and associated pain.

Other RF conductive methods may use two-point contact electrodes, but such methods cause undue penetration of thermal energy into tissue surrounding the desired region of application. Regardless of whether such RF devices include one or two electrodes, the radio frequencies that are currently used to generate thermal energy are in the range of approximately tens of kilohertz to approximately one megahertz. Thermal energy arising from these frequencies results in ionic drag, rather than dielectric heating.

RF energy, when introduced to tissue, induces eddy currents in the tissue. These eddy currents are created by the changing electromagnetic field of the RF energy which acts on the electrons and ions in the tissue. The tissue has some finite resistance just like any conductive material, like an electrical wire. The tissue "resists" the flow of these eddy currents dissipating the energy as heat.

Prior balloon ablation catheters designed for use in renal denervation procedures have certain limitations. For example, WO 2012/061150 describes a balloon catheter system using static frequency selections of 915 MHz, 2.5 GHz, or 5.1 GHz, whereas an embodiment of a balloon catheter apparatus and associated system disclosed in the instant application uses phase shifting and/or frequency sweeping to optimize therapeutic results. Further, the static frequency antenna designs described in WO 2012/061150 have limited frequency bandwidth and thus require variable tuning between different patients due to the variability of the dielectric properties of patient tissues and fluids. As such, where existing designs may operate at sub-optimal tuning characteristics, an embodiment of a balloon catheter apparatus disclosed herein contains an emitter that is relatively broad-band and thus can readily adapt to variability in patient anatomy and body chemistry. Moreover, the phase shifting and/or sweeping feature disclosed herein allows for a balloon catheter system of the type herein described to deliver microwave energy to tissue at different radial depths, while avoiding dielectric-related thermal peaks in RF absorbing tissue or fluids. WO 2012/061150 further limits its target tissue at a depth less than 5 millimeter radially from the center of the renal artery. By contrast, an embodiment of a balloon catheter apparatus and associated system disclosed herein targets tissue in the range of about 0.5 mm to about 12 mm radially from the inner surface of the artery wall. Further, an embodiment of a balloon catheter apparatus and associated system disclosed herein is configured to operate in any vessel—not only the renal artery as described in WO 2012/061150.

Hypertension exacerbates nephropathy and other cardiovascular disease states. Chemical treatment of hypertension via angiotensin II receptor blockers and angiotensin-converting-enzyme inhibitors have limited efficacy and are associated with certain adverse events that limit the eligible patient population. Therefore, any treatment that can reduce hypertension and its associated consequences would be welcomed by the medical community.

SUMMARY

A balloon catheter apparatus and associated system is disclosed, comprising an elongated shaft having a proximal end, a distal end, and adapted for positioning in an artery; an emitter capable of emitting microwave energy positioned at the distal end; an inflatable balloon associated with the emitter at the distal end may be configured to allow blood to pass through the artery while the balloon is inflated; and a control system at the proximal end.

The balloon catheter apparatus and associated system is designed to be capable of tissue ablation via delivery of microwave energy from the emitter to targeted tissue. The targeted tissue is located in the range of about 0.5 millimeters to about 12 millimeters radially outward from an inner surface of the artery. In renal denervation procedures, the targeted tissue may include one or more sympathetic nerves.

The balloon catheter apparatus and associated system may be intravascularly introduced into a patient's body and advanced via the patient's vasculature to the point of operation. In renal denervation procedures, the point of operation is in the renal artery, including accessory renal arteries and secondary renal arteries, or aorta.

The emitter may include one or more antennas. When a plurality of antennas is employed, the antennas may be configured in an array. The microwave energy radiating from the emitter can form a volumetric field toward the targeted tissue. When activated, the emitter is able to emit microwave energy in a plurality of 15 to 600 second pulses. The duration of the pulses can be modulated by the user if desired for a particular patient or procedure. The emitter is capable of emitting microwave energy in broad band frequencies. Further, the emitter is capable of phase shifting or frequency sweeping to optimize the microwave energy delivery.

The inflatable balloon of the balloon catheter apparatus and associated system may contain channels to avoid vascular occlusion. These channels form a passage for fluids between the arterial wall and an inflated balloon and may be in a spiral configuration.

The interior and/or exterior of the inflatable balloon may be coated with shielding material. The shielding material may be applied to the balloon in such a manner where the absence of the shielding material forms slots. These slots can be used to directionally focus electromagnetic waves originating from the emitter. Shielding material can also be used to protect non-targeted tissue from microwave energy and associated heat.

Alternatively, or in addition to the use of shielding material, non-targeted tissue may be thermally protected by the use of coolants with the balloon catheter apparatus and associated system. The balloon catheter and associated system may comprise one or more lumens or coolant channels wherein a coolant can be introduced from the proximal end of the balloon catheter apparatus and associated system to the distal end. The coolant may include a dielectric agent, including fluids and gases. One or more central lumens may form channels within the wall of the balloon. When the coolant is only delivered and circulated within the one or more lumens within the walls of the balloon, the coolant does not contact the emitter. One or more central lumens are also capable of delivering and circulating fluid to and from an area associated with the emitter whereby the dielectric agent contacts the emitter. Fluid coolant can also be introduced to the patient's vasculature through irrigation ports in communication with one or more central lumens located within the catheter shaft.

The balloon catheter apparatus may also include an emitter channel. The emitter channel forms a path for the emitter to follow when the user desires to treat tissue longitudinally. The emitter channel may also contain coolant fluid or gas. The balloon catheter apparatus may further comprise a manipulation wire for moving the emitter along the emitter channel. The emitter channel may form a linear or spiral path within the inflatable balloon and the emitter can be positioned and moved along those paths to treat tissue longitudinally.

The balloon catheter apparatus and associated system comprises a control system capable of monitoring the energy delivered and temperature generated and may be programmed to alter the delivery of energy if certain power and temperature parameters are exceeded. In some cases, the energy alteration may include a reduction in the microwave energy delivered. In still other cases, the energy alteration may include altering the frequency, altering the frequency phase shift, or both. In other cases, the rate or pressure or flow of the coolant may be adjusted. In other cases, the energy alteration may include ceasing all microwave energy delivery. The balloon catheter apparatus and associated system comprises a control system capable of monitoring pressure within the balloon and providing real-time feedback of any pressure changes within the balloon. Exemplary pressure-sensing monitors may comprise monitors located within the inflatable balloon or monitors associated within the pump infusing fluid or gas to inflate the inflatable balloon.

A user may employ an embodiment of a balloon catheter apparatus and associated system in a method of treating a patient via ablation of a targeted tissue. In one embodiment, a method comprises the steps of: intravascularly positioning a catheter having an emitter within an artery of the patient; activating the emitter such that microwave energy is produced and transferred from the emitter to the targeted tissue; and treating the targeted tissue with a balloon catheter apparatus and with enough microwave energy to therapeutically impair the targeted tissue of the patient.

In another embodiment, a method of renal denervation of a targeted tissue of a patient is disclosed, the method comprising the steps of: intravascularly positioning a catheter having an emitter within an artery of the patient; activating the emitter such that microwave energy is produced and transferred from the emitter to the targeted tissue; and treating the targeted tissue with a balloon catheter apparatus and with enough microwave energy to therapeutically impair one or more renal nerves of the patient.

As one skilled in the art can appreciate, treating targeted tissue with microwave energy results in a functional impairment of the treated targeted tissue such that the functional impairment has a therapeutic benefit for the patient.

A user may operate an embodiment of a balloon catheter and associated system in a manner whereby the targeted tissue is treated with a dose of microwave energy at only one location of placement of the inflated balloon. In addition, a user may utilize a manipulation wire attached to the emitter, which wire may be pulled toward the user or advanced away from the user while the emitter is emitting microwave energy to treat tissue longitudinally or rotationally without the need to deflate the balloon or reposition the balloon catheter apparatus. The emitter may be positioned and moved along an emitter channel formed in the balloon. The emitter channel may form a linear or spiral path for moving the emitter therein.

A balloon catheter apparatus and associated system is disclosed, comprising a catheter configured to house a flexible coaxial cable, a lumen used for a guide wire, and a sensor cable, wherein the coaxial cable and the sensor cable are in communication with a control system, and wherein the sensor cable is in communication with a sensor, for example, a thermistor or optical temperature sensor; an inflatable balloon located at the distal end of the catheter, the inflatable balloon comprising a length of 10 millimeters to 35 millimeters and capable of expanding to an outside diameter of 4 millimeters to 8 millimeters; a slot antenna positioned in the inflatable balloon and in communication with the coaxial cable, the antenna configured to emit microwave energy to a target tissue zone located 0.75 millimeters to 6.0 millimeters from an inner wall of a renal artery, wherein the antenna is radially centered in the inflatable balloon and located within a proximal half of the inflatable balloon, wherein tissue within the target tissue zone is heated to a temperature between 48° C. and 65° C. by the application of microwave energy; at least one irrigation port located at the distal end of the balloon catheter apparatus configured to allow a fluid to exit the balloon catheter apparatus after the fluid has cooled elements of the balloon catheter apparatus and tissue outside the target tissue zone that may be heated as a consequence of delivering microwave energy from the antenna; and a control system comprising: a fluid pump configured to introduce fluid into a proximal end of the catheter at a flow rate of between 25 mL/min and 150 mL/min to maintain inflation of the balloon; a power amplifier capable generating microwave energy for delivery to the target tissue zone for at least one energy application cycle ranging from 60 seconds to 240 seconds at a frequency within the range of 2.4 GHz and 2.5 GHz; a computer system capable of monitoring and regulating the delivery of microwave energy, the fluid pump, the sensor and antenna reflected power, wherein the computer system is programmable with a safety algorithm to ensure the balloon catheter apparatus is operating within acceptable temperature and power ranges. In some embodiments, the control system can alter the frequency within the range of 2.4 GHz to 2.5 GHz. Other embodiments of the balloon catheter apparatus and associated system are disclosed herein.

A microwave ablation system is disclosed, comprising: a balloon catheter apparatus and a control system. The balloon catheter apparatus comprises (1) a catheter configured to house a coaxial cable and one or more coolant channels, (2) an inflatable balloon located at the distal end of the catheter, and (3) an antenna positioned in the inflatable balloon and in communication with the coaxial cable. The inflatable balloon comprises a length of 10 to 45 millimeters. The antenna is configured to emit microwave energy to a target tissue zone located within a range from 0.5 millimeters to 12.0 millimeters radially from an inner wall of an artery, where tissue within the target tissue zone is heated by the emitted microwave energy to a temperature from 40° C. to 100° C., and where the one or more coolant channels are configured to cool one or more elements of the microwave ablation system and/or non-targeted tissue lying outside the target tissue zone that may be heated as a consequence of emitting microwave energy from the antenna. The control system comprises (1) a fluid pump configured to introduce fluid into a proximal end of the catheter, (2) a power amplifier capable of generating microwave energy for delivery to the target tissue zone for at least one energy application cycle ranging from 60 seconds to 600 seconds at a frequency ranging from 2.4 GHz to 2.5 GHz, and (3) a computer system configured to monitor and/or regulate the delivery of microwave energy to the target tissue, the fluid pump, at least one sensor, and antenna reflected power, wherein the computer system comprises a safety algorithm to ensure the microwave ablation system operates within acceptable temperature and power ranges.

The target tissue zone may be heated by the emitted microwave energy to a temperature ranging from 48° C. to 75° C.

The inflatable balloon when inflated may include a tapered geometry. The inflatable balloon when inflated may include a non-symmetric geometry.

The one or more coolant channels may include at least two coolant channels to form a circulation loop to continuously cool the balloon catheter apparatus and/or non-targeted tissue. In one embodiment, saline may be conveyed by the one or more coolant channels. In one embodiment, carbon dioxide may be conveyed by the one or more coolant channels. In one embodiment, Ringers solution may be conveyed by the one or more coolant channels.

The at least one application cycle may contain more than one pulse of microwave energy. The computer system may be configured to monitor a pressure of fluid in the one or more coolant channels and adjust a flow rate and/or fluid volume output of the fluid pump. The one or more coolant channels may be in communication with an irrigation port configured to deliver fluid to the patient's vasculature after the fluid has cooled elements of the balloon catheter apparatus and/or non-targeted tissue.

The catheter may include a lumen positioned adjacent the coaxial cable and be configured to receive a guide wire. The coaxial cable may include a central lumen configured to receive a guide wire and to transport fluid to the balloon. One of the one or more coolant channels may be located inside the coaxial cable.

A distal portion of the catheter may be more flexible than a proximal portion of the catheter. A distal portion of the coaxial cable may be more flexible than a proximal portion of the coaxial cable.

The catheter may include one or more sensors connected to one or more sensor cables and the one or more sensor cables may be in communication with the control system.

The catheter may include a radiometer. The antenna may be configured to receive reflected radiation information from the target tissue zone, and transmit the radiation information to the control system via the coaxial cable. The target tissue zone may be located within a range from 0.75 millimeters to 5.0 millimeters radially from the inner wall of the artery.

The control system may be capable of phase shifting the emitted microwave energy. The control system may be capable of frequency sweeping the emitted microwave energy. The antenna may be a slot antenna, a multi-slot antenna, or a choked slot antenna. The control system may be configured to permit selection of a predetermined dose amount of microwave energy from among a plurality of predetermined dose amounts of microwave energy to be emitted by the antenna.

A method of treating a patient with cardiac arrhythmias via ablation of cardiac tissue is disclosed, comprising the steps of: (1) intravascularly positioning a catheter having an emitter within a vein of the patient, (2) emitting microwave energy from the emitter to the cardiac tissue, and (3) treating the targeted tissue with a microwave ablation system described herein and with enough microwave energy to therapeutically impair the targeted cardiac tissue of the patient while not damaging non-targeted tissue.

A method of treating a patient via ablation of a targeted tissue is disclosed, comprising the steps of: (1) intravascularly positioning a catheter having an emitter within an artery of the patient, (2) emitting microwave energy from the emitter to the targeted tissue, and (3) treating the targeted tissue with a microwave ablation system described herein and with enough microwave energy to therapeutically impair the targeted tissue of the patient while not damaging non-targeted tissue.

In one embodiment of the method, the patient may suffer from pulmonary hypertension and the targeted tissue may be sympathetic and/or parasympathetic nerves. In another embodiment of the method, the patient may suffer from Type I or Type II diabetes and the targeted tissue may be sympathetic and/or parasympathetic nerves. In another embodiment of the method, the patient may suffer from chronic kidney disease and the targeted tissue may be sympathetic and/or parasympathetic nerves. In another embodiment of the method, the patient may suffer from sleep apnea and the targeted tissue may be sympathetic and/or parasympathetic nerves. The method may include the step of selecting a predetermined dose amount of microwave energy from among a plurality of predetermined dose amounts of microwave energy prior to emitting microwave energy from the emitter.

BRIEF DESCRIPTION OF THE DRAWINGS

FIG. 4 illustrates a distal end view of the inflatable balloon of the balloon catheter apparatus shown in FIG. 3.

FIG. 5 illustrates a side view of the inflatable balloon of the balloon catheter apparatus shown in FIG. 3.

FIGS. 24A, 24B, and 24C illustrate an embodiment of a non-symmetrical inflatable balloon of the balloon catheter apparatus.

FIGS. 26A, 26B, and 26C illustrate another embodiment of a non-symmetrical inflatable balloon, a tapered inflatable balloon, of the balloon catheter apparatus.

DETAILED DESCRIPTION

Figure 1:
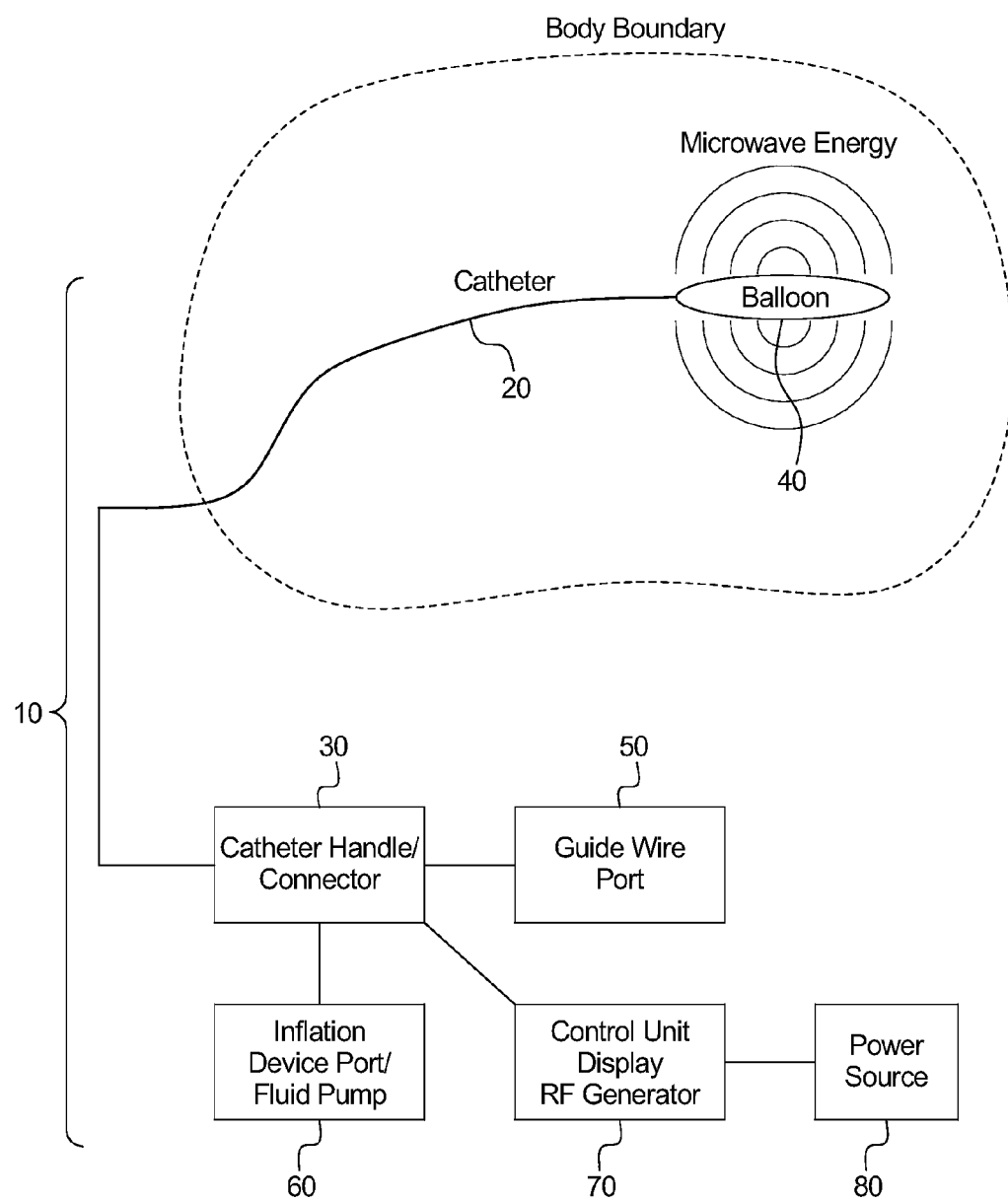
FIG. 1 is a diagram of one embodiment of a balloon catheter apparatus located within the patient's body boundary and an associated system located outside the patient's body boundary.

The description that follows describes, illustrates and exemplifies one or more particular embodiments of a balloon catheter apparatus and method of use for treating disease. This description is not provided to limit the disclosure to the embodiments described herein, but rather to explain and teach various principles to enable one of ordinary skill in the art to understand these principles and, with that understanding, be able to apply them to practice not only the embodiments described herein, but also other embodiments that may come to mind in accordance with these principles. The scope of the instant disclosure is intended to cover all such embodiments that may fall within the scope of the appended claims, either literally or under the doctrine of equivalents.

It should be noted that in the description and drawings, like or substantially similar elements may be labeled with the same reference numerals. However, sometimes these elements may be labeled with differing numbers in cases where such labeling facilitates a more clear description. Additionally, the drawings set forth herein are not necessarily drawn to scale, and in some instances proportions may have been exaggerated to more clearly depict certain features.

A percutaneous transluminal balloon catheter apparatus and associated system is disclosed for treating disease. In one embodiment, the balloon catheter apparatus and associated system can be used for treating cardiovascular hypertension. To treat cardiovascular hypertension, the balloon catheter apparatus and associated system may be implemented as part of a renal denervation procedure on a patient. As described more fully below, such apparatus and associated system comprises a balloon catheter comprising an emitter to emit electromagnetic waves in the microwave frequency spectrum in close proximity to one or more renal neural fibers and thermally disrupt the fibers sufficient to block neurological signals from passing therethrough—while causing no unintended damage or injury, or at most only inconsequential damage or injury, to the patient's renal or cardiovascular vasculature and surrounding organs or tissue. In a further embodiment, the balloon catheter apparatus and associated system may be used for treating Hypertension, including Pulmonary Hypertension, Insulin Resistance, Diabetes, Diabetic Nephropathy, Chronic Kidney Disease, Congestive Heart Failure, Hepatorenal Syndrome, End-Stage Renal Disease, and Acute Renal Disease. In yet a further embodiment, a modified balloon catheter apparatus and associated system may be used to treat Atrial Fibrillation, Sleep Apnea, Obesity, Polycystic Ovary Syndrome, Sarcomas, Carcinomas, COPD, and Lymphomas.

In some embodiments, one or more diseases can be treated by delivering microwave energy from the balloon catheter apparatus and associated system to the upper and/or lower Renal Sympathetic Nerve Plexus. Whether to target the upper, lower, or a combination of both Renal Sympathetic Nerve Plexus depends on the desired amount of ablation and degree of desired disruption of renal sympathetic nerve activity. One of ordinary skill would appreciate when total ablation is desired in certain diseases and/or patient populations and when less than total ablation is desired.

The balloon catheter apparatus and associated system as described herein can be adapted to treat a particular disease for a given patient by varying the degree of the ablation and by targeting a variety of tissue. For example, the balloon catheter apparatus and associated system can target tissue at various depths as needed to treat a particular disease for a particular patient.

"Treating" in the present disclosure includes alleviating symptoms, arresting, slowing, retarding, or stabilizing progression of a condition or a physiological or morphological marker thereof, and/or improvi clinical outcome, for example as measured by blood pressure, quality of life, incidence or severity of adverse cardiac events, or survival time. One skilled in the art would appreciate what morphological markers and/or indicators of clinical outcomes would be appropriate for the contemplated diseases. By way of example, an improvement of estimated glomerular filtration rate (eGFR), either by increasing eGFR or slowing the rate of decline, would be an indicator of renal function and an appropriate measure for treatment of renal diseases.

In one embodiment, energy in the form of electromagnetic waves is delivered via a balloon catheter apparatus and associated system to sympathetic nerves associated with a renal artery. The electromagnetic waves are emitted at a predetermined frequency range from an emitter positioned in or on the balloon portion of a balloon catheter apparatus. The emitter may include one or more emitters. Each emitter may include an antenna or an antenna array.

In one embodiment, the emitter is configured to provide radiation symmetry 360° about a central axis of the artery to allow energy in the form of electromagnetic waves to treat a predetermined radial depth at a particular longitudinal location in the artery. This radiation pattern avoids the need to rotate the balloon or emitter to emit energy multiple times to complete an ablation procedure and minimizes exposure to the patient of unnecessary radiation. By emitting radiation 360° from the emitter, the electromagnetic waves radiate radially in all directions about the central axis to create a volumetric field of electromagnetic radiation that excite tissue at a predetermined radial depth from the inner wall of an artery. The excited tissue locally increases in temperature due to the presence of the electromagnetic radiation. In the case of renal denervation ablation procedures, the excited tissue includes renal nerves. When the renal nerves absorb the microwave energy from the emitter, the signal transduction of the nerves is altered and the patient receives a therapeutic benefit therefrom. By focusing electromagnetic wave energy at a particular radial distance of the emitter, conduction of thermal energy may begin at the focused location and proceed radially inward, radially outward, and longitudinally along the artery wall as the case may be. The emitter is capable of delivering energy in broad band frequencies.

In one embodiment, the emitter is advanced into the renal artery before activating the emitter. In another embodiment, the emitter is advanced into the aorta, in cranial proximity to the renal artery, before activating the emitter.

Various embodiments of the balloon catheter apparatus may have the emitter located on the centerline of the catheter or extended to a desired position within the inflated balloon during energy delivery. The emitter can deliver energy from a static location or while traversing longitudinally along either a linear or a spiral path. The emitter may be advanced in one or more emitter channels formed into the balloon surface for precision delivery. The emitter channels may also be formed by materials within the balloon. In one embodiment, the emitter channel forms a linear path for the emitter along the longitudinal centerline axis of the balloon. In another embodiment, the emitter channel is a path off-center the centerline axis of the balloon. In a further embodiment, the path off-center the centerline axis of the catheter is a spiral path. The user may vary the position of the emitter through use of a manipulation wire. The manipulation wire may be used manually or associated with a control system which mechanically or electromechanically advances and/or retracts the manipulation wire according to the user's needs.

In one embodiment, an emitter comprising an antenna includes multiple antenna segments, patches, rings, or other simple or complex shapes to focus the radiated energy to a predetermined radial depth to target the distribution of energy to an intended tissue or portion thereof. The antenna may include design features that spread its useable frequency range to allow adjusting, phasing, or sweeping the frequency of the antenna feed signal while maintaining the antenna efficiency and impedance matching. This adjusting, phasing, or sweeping enables the ablation catheter system to treat tissue at different radial depths while minimizing exposure to untargeted tissue. Treating tissue at different radial depths can allow the user to ablate a larger amount of desired targeted tissue in a controlled manner. A further benefit of frequency sweeping includes minimizing hot spots along the cable by distributing energy along the length of the catheter. Another benefit of frequency sweeping is to improve the life and efficiency of the cable. Another benefit of frequency sweeping is a reduction in reflected power due to physiologic variables, for example, tissue impedance.

In one embodiment, the antenna may comprise two or more emitting elements with methods to phase relate each emitting element's radiated electromagnetic waveform to allow steering or focusing of the transmitted energy, in order to concentrate heating effects of the emitted energy at targeted tissue depths.

The antenna may comprise cylindrical, conical, biconical, planar, triangular, slot, multi-slot, choked slot, or multilayer geometries and structures where adjacent layers have different shapes and are separated by dielectric layers. Alternatively, the antenna may also include complex curvatures rather than being simple cones or triangles, for example.

In one embodiment, a plurality of antennas can be contained within the balloon. These antennas could be arranged in a particular array which may be ideal for a particular procedure.

In various embodiments, the antenna may include a printed circuit board, a Low (or High) Temperature Cofired Ceramic (LTCC or HTCC), micro-machined structures, molded or over-molded structures, swaged structures, structures plated on or laminated over elastomer or plastic substrates, and/or small die cast or die formed structures.

The antenna may include features or structures surrounding the antenna to create focusing or "slotting type" effects. "Slotting type" refers to slots formed within the balloon that focus or target the RF energy radiation or circumferential RF energy radiation. To achieve this "slotting type" effect, one or more portions of the balloon may also include a coating that is configured to shield electromagnetic waves emitted from the antenna to directionally configure the microwave transmission pattern to tissue outside of the balloon. Either the interior or exterior of the balloon may be coated with material designed to shield RF energy, effectively prohibiting RF energy to be transmitted except through the slots formed by the absence of shielding material. These slots may be designed according to the needs of a particular procedure. Portions of the shielding material can be removed in a desired pattern to allow RF energy to pass through tissue outside the balloon in accordance with the removed designed pattern. For example, shielding material may be placed in a configuration to avoid heating blood passing therethrough. In another embodiment, the shielding material is positioned to avoid heating cooling fluids or contrast media or agents passing therethrough.

The shielding material may include reflective or absorptive materials, or a combination of both. Shielding materials as described may include dielectric, semi-conducting, or conducting materials, which encompass cast material, coated material, encapsulated material, or formed material. Such material may be composed of metal, ceramic, glass, ferrite, plastic, elastomer, or other suitable materials, including chemical compounds and mixtures of diverse materials.

The antenna and associated balloon catheter apparatus may accommodate a broad range of artery sizes to prevent requiring the operator to use structurally different antennae with different patients. For example, the balloon for use in renal denervation procedures where the balloon catheter apparatus is advanced into the renal artery can have a diameter in the range or about 2.0 to about 12.0 millimeter and a length in the range of about 10 to about 45 millimeter. As a further example, the balloon for use in renal denervation procedures where the balloon catheter apparatus is advanced into the aorta can have a diameter in the range or about 22 to about 46 millimeter and a length in the range of about 10 to about 60 millimeter. This may or may not still require different catheters having different, selectable inflated balloon size to account for differences in artery anatomy or geometry between patients.

The balloon catheter apparatus and associated system disclosed herein contemplates the use of coolant and heat transfer mechanisms to promote blood circulation past the balloon and/or minimize thermal damage to untargeted tissue.

Local heating of the emitter, device, or immediate vicinity of the device may result if the emitter is immersed in ionic fluids while the emitter is emitting electromagnetic radiation. To optimize the energy delivery and to maintain a desired temperature range of the emitter during operation, the emitter may be immersed in an appropriate dielectric agent. By immersing the emitter in a dielectric agent, surrounding, untargeted tissue may be better protected from unintended thermal damage. Preferred dielectric agents include, but are not limited to, non-ionic contrast media, Carbon Dioxide ($CO_2$) or other deionized fluid or gas having a low dielectric constant. In one embodiment, a nonionic, dielectric cooling fluid may be circulated to, from, and within the balloon to cool the inner artery walls and to maintain a desired temperature range during operation. In one embodiment, the dielectric agent may comprise some or all of the desirable effects of a "contrast media," such as the contrast media or agents used in X-ray procedures. In another embodiment, the $CO_2$ gas may be chilled to supercritical temperatures before introduction into the balloon catheter apparatus. When supercritical $CO_2$ is utilized, the emitter may deliver higher frequency microwave energy ranging from 8 to 10 GHz to optimize the ablation depth and rate of ablation. A non-ionic contrast media or other dielectric agent having lower conductivity and lower dielectric constant than tissue or blood may be used to inflate the balloon and/or circulate in the balloon. The balloon may also be attached to a fluid or gas pump which circulates the dielectric agent within the lumen of the balloon to act as a cooling mechanism for the interior wall of the artery.

When a gas is used as a dielectric agent, the gas will be contained within the balloon catheter apparatus and will not be introduced into the patient's vasculature. When a fluid is used as a dielectric agent, the fluid optionally can be introduced into the patient's vasculature through irrigation ports. In some embodiments, more than one dielectric agent can be employed, including, but not limited to, one gas and one fluid or two fluids.

In one embodiment, a dielectric agent may be circulated to, from, and within the walls of the balloon to achieve the desired cooling effect of the adjacent tissue. In this embodiment, the dielectric agent would not contact the emitter. In a further embodiment, the dielectric agent may be introduced into the lumen of the balloon, contacting the emitter, as well as in cooling channels within the balloon walls. In yet a further embodiment, a dielectric agent in the form of a fluid can be injected into the bloodstream via irrigation ports positioned on or near the balloon of the balloon catheter apparatus to protect the arterial wall against thermal damage by directly cooling the arterial wall and serving as a heat transfer mechanism to pull the heat away from the procedure site following the bloodstream. These irrigation ports may be located at the distal tip of the balloon catheter apparatus, on the balloon of the balloon catheter apparatus, at the junction formed between the distal tip and the balloon of the balloon catheter apparatus, or proximal of the inflatable balloon of the balloon catheter apparatus. Irrigation ports may be terminated with a one-way valve or open to the bloodstream without a valve. In some embodiments, the lumen carrying the dielectric agent that serves as a coolant may also receive a guide wire for use in positioning the balloon within a patient. The irrigation port is located in vivo once the balloon catheter apparatus is in place and the emitter is adjacent the target tissue. In embodiments where the dielectric agent is in contact with the emitter, the irrigation ports form an exit to allow the dielectric agent to transport heat away from the emitter that is generated during operation. In other embodiments, the irrigation ports serve as an exit for a dielectric agent that has cooled the balloon catheter apparatus as the balloon catheter apparatus can increase in temperature while or soon after delivering energy as described herein.

In some embodiments, a dielectric agent passes through the catheter in a lumen shared by or adjacent to the cable whereby the dielectric agent cools the cable throughout the catheter. In these embodiments, the cable of the balloon catheter apparatus can operate at power capacities above the rated capacity.

In some embodiments, dielectric agents can include saline, Ringer's solution, or other medical-grade hydration or contrast agents with low ionic strength provided that the inflatable balloon catheter apparatus and associated system functions in ablation procedures described herein and is not hindered by the presence of low concentration ions.

In some embodiments, the cable comprises an inner electrical conductor configured in the shape of a tube, the inner diameter of which forming a central lumen. The central lumen is configured to transport fluid or gas therethrough to the balloon for: (1) cooling a microwave emitter, such as an antenna, positioned in or on a wall of the balloon, (2) cooling the wall of the central lumen, which wall is formed by an inner electrical conductor, and (3) inflating the balloon. The central lumen is also configured to (1) receive a guide wire therethrough for positioning the catheter in a vessel, and (2) receive pressure and temperature devices therethrough for communicating pressure and temperature data from or in the vicinity of the balloon and/or along the lumen to the proximal end of the catheter. In these embodiment, the inner diameter surface of the inner conductor is not covered with any material and is configured to directly contact the cooling fluid or gas that is transported therethrough to the balloon. In operation, the flow rate through the central lumen is 10 ml/min to 150 ml/min.

The flow of a dielectric agent through the balloon catheter apparatus can be a consistent infusion, a bolus controlled by the user, or a combination thereof.

In some embodiments, a dielectric agent would be cooled to an external temperature of 0° C. to 37° C. before introduction into the balloon catheter apparatus and associated system. In embodiments where cooled $CO_2$ is employed, the $CO_2$ may be cooled to subzero temperatures. In some embodiments, the dielectric agent would be circulated for constant cooling of the dielectric agent.

In other embodiments, a dielectric agent may be cooled to an external temperature less than 0° C. before introduction into the balloon catheter apparatus and associated system.

The use of a dielectric agent as a coolant in the embodiments described herein prevents inflammation and other adverse events associated with prior existing artery stenosis, plaque, or other conditions that may be exacerbated by local increased temperature.

The balloon may also have a spiral configuration with channels that form a passage for blood to pass through and bypass the balloon when the balloon is inflated in a vessel. The blood passing between the vascular wall and through the balloon channels effectively acts as a heat transfer mechanism to draw heat away from the balloon catheter apparatus while energy is being delivered by the emitter. Use of flowing blood to transport heat away from the vascular wall protects the non-targeted tissue, such as the vessel inner wall, from thermal damage associated with any ablation procedure, whether by RF, thermal, microwave, or any other form of energy radiation. A blood pass-through channel may also be incorporated into the lumen of the catheter body. Allowing the blood to continue to flow during the ablation procedure minimizes the risk of thrombosis, scarring, ischemia, and/or stress on the patient's vascular system. A balloon catheter apparatus employing a spiral balloon configuration can also include the use of one or more dielectric agents as described herein to provide supplemental heat transfer away from non-targeted tissue. In addition to minimizing possible adverse events while operating the balloon catheter ablation system, allowing blood to flow through the artery while the balloon is inflated will also assist in optimizing the balloon catheter ablation system by moderating temperatures and reducing temperature gradients in the vicinity of heat-generating components within the balloon catheter apparatus.

The balloon of the inflatable balloon catheter may be 10 millimeters to 40 millimeters in length. The inflated balloon ranges from 2 millimeters to 35 millimeters in diameter depending on the intended area of operation within a patient. In some embodiments, the inflated balloon diameter may vary along the length of the balloon to form different geometries. For example, the inflated balloon may form a tapered geometry to accommodate a tapered artery geometry. The balloon may be compliant, semi-compliant, or non-compliant. An emitter or various sensors disclosed herein can be incorporated into the wall of the balloon, for example, an emitter and/or sensor(s) can be located on the interior wall of the balloon, on the exterior of the balloon, within the walls of the balloon, or some combination thereof. The balloon portion may include devices or systems, such as radiopaque markers which are visible under fluoroscopy, to help ensure the balloon is properly positioned within the artery so that the balloon outer wall is at or near a target longitudinal and diametrical position within the artery. In one embodiment, the radiopaque markers are located on a surface of the balloon. In other embodiments, the radiopaque markers are located distal or proximal to the balloon. In another embodiment, the radiopaque markers are located internal to the balloon along the catheter shaft. In further embodiments, the emitter may be radiopaque. In still further embodiments, the balloon can be filled with a radiopaque contrast media to assist the end user in locating and positioning the emitter. Use of such radiopaque devices or systems may help ensure proper alignment and centering of the emitter. Furthermore, the markers may help prevent pools of blood in unwanted regions, such as between the balloon and the artery wall. The balloon and/or catheter materials may also include materials that can be visualized in vivo via X-ray to ensure proper positioning and use. Visualization materials may comprise particle suspensions or material solutions containing high-density elements or compounds containing such elements, which might include tantalum, tungsten, platinum, iridium, gold, rhenium, or other high-density elements. Further marker structures of discrete shapes made of X-ray absorbing materials may also be molded into or onto the balloon, catheter, or other locations in the assembly to obviate use of contrast media.

The emitter and associated system may be tuned and/or calibrated to radiate electromagnetic waves at a frequency among a range of frequencies in, for example, the microwave spectrum. The specific emitted frequency and the range of desirable frequencies that may be emitted to disrupt the sympathetic nerves in a renal denervation procedure may be determined by balancing the amount of energy that will be absorbed by tissue at a desired range of target radial distances from the emitter while accounting for a patient's body to act as a shield to prevent unwanted emissions in, for example, the microwave spectrum to other untargeted tissues in the body or externally to the body. The choice of emitted frequency helps determine the physical size of the emitter for electromagnetic wave emissions as well as the predicted bulk absorption rate by the arterial wall and surrounding tissue of the emitted frequency.

Microwave frequencies in tissue are absorbed at rates determined by tissue characteristics and by microwave frequencies. In general, higher microwave frequencies are absorbed in a shorter distance than lower microwave frequencies. By configuring the appropriate microwave frequency, the desired energy heating penetration depth in tissue may be achieved in order to ablate targeted tissue or disrupt targeted nerves in the desired volume while minimizing the effect on non-targeted nerves and other non-targeted tissue outside the treatment volume.

Consequently, microwave frequencies in the range of about 500 MHz to about 50 GHz, and more particularly of about 500 MHz to about 30 GHz, may be used to thermally disrupt or ablate sympathetic nerves without incurring unintended damage or injury, or at most only inconsequential damage or injury, to the patient's vasculature and surrounding tissue.

In one embodiment, a predetermined frequency range causes the electromagnetic wave energy emitted to be absorbed by tissue in the first several millimeters of tissue radially from the position of the antenna. As will be appreciated by those skilled in the art, the depth of energy absorption will depend on frequency, relative permittivity of the tissue, power of the microwave energy, and tissue temperature (indirectly by changing relative permittivity of the tissue). In one embodiment, the balloon catheter apparatus and associated system emits microwave energy at frequencies at about 500 MHz to about 30 GHz, more particularly at about 5.0 GHz to about 19.5 GHz, to thermally disrupt sympathetic nerves in local tissue nominally located approximately 0.5 millimeter to approximately 10 millimeter radially from the inner wall of an artery. In one embodiment, the balloon catheter apparatus and associated system emits microwave energy at frequencies at about 500 MHz to about 30 GHz, more particularly at about 5.0 GHz to about 19.5 GHz, to thermally disrupt sympathetic nerves in local tissue nominally located approximately 0.5 millimeter to approximately 10 millimeter radially from the inner wall of the renal artery when positioned within the renal artery in the vicinity of a patient's kidney. In another embodiment, the balloon catheter apparatus and associated system emits microwave energy at frequencies at about 500 MHz to about 30 GHz to thermally disrupt sympathetic nerves in local tissue nominally located approximately 0.5 millimeter to approximately 10 millimeter radially from the inner wall of the aorta when positioned within the aorta proximal to the patient's renal artery. In one embodiment, a user determines and selects an initial frequency to be emitted. In another embodiment, the initial frequency to be emitted is not user-selectable. In one embodiment, a user configures a plurality of the parameters that are desired for a denervation or ablation dose. In another embodiment, a plurality of the parameters for a desired denervation or ablation dose are predetermined or are configured automatically by a computer algorithm.

Other means of renal denervation may include selectively heating the sympathetic nerves cells while having minimal effect on the surrounding tissue in the presence of microwave energy. This can be achieved by selecting a frequency, phase, and power setting, or combination thereof to correlate to the specific dielectric properties of the nerve tissue as opposed to the surrounding tissue. The dielectric loss factor and/or energy absorption characteristics of the two different types of tissues will determine the degree to which microwave energy will be converted to heat at the target site. The dielectric loss factor and/or energy absorption characteristics are frequency, phase, and power dependent and peak heating of the tissue can be achieved by selecting the appropriate parameters which correspond to the target tissue exhibiting the highest dielectric loss.

Microwave energy radiates from the emitter outward through the balloon and into tissue, where tissue absorbs the energy at some percentage per travel distance, and the radiated waves expand roughly radially from the emitter. Choice of frequency and emitter configuration may allow either a non-symmetrical or a symmetrical wave energy absorption pattern around the balloon axis of symmetry. In one embodiment the desired thermal effect zone (i.e., the targeted tissue), where nerve damage is induced but scar tissue is not formed, is approximately 0.5 millimeter to approximately 10.0 millimeter radially outward from the inner wall of an artery. In another embodiment, the desired thermal effect zone is approximately 0.5 mm to approximately 12.0 mm, or 0.75 mm to 5.0 mm, radially outward from the inner wall of the artery. Frequency, power, transmit duty cycle, internal coolant application, and treatment period may be varied to obtain target temperatures in tissue in this targeted depth region. In preferred embodiments, the targeted tissue is the core density of nerves, which are located about 2.0 millmeters to about 4.0 millimeters radially outward from the inner wall of an artery. One skilled in the art would appreciate that some patients may have unique anatomies where the core density of nerves may lie outside the range of about 2.0 millimeters to about 4.0 millimeters. Thus, an adjustment of at least one of the frequency, power, transmit duty cycle, internal coolant application, and treatment period may be made to accommodate the unique anatomy of a given patient. In one embodiment, substantially all of the electromagnetic wave energy is transferred to and absorbed by tissue within the first few millimeters of tissue radially outward from the balloon, thereby minimizing adverse effects on other body organs or tissue.

In addition to the selection of a predetermined initial frequency within a predetermined range of frequencies to generate electromagnetic waves for emission by the emitter, a computer control unit may also provide phase shifting and/or frequency sweeping features to improve energy distribution and targeting within the artery tissue by preventing phase-dependent peaks and valleys of energy at various radial depths from the point of emission of the energy. In one embodiment utilizing frequency sweeping, a computer control unit may alter delivered frequencies within a 2 GHz bandwidth of the initial frequency, once or several times, thereby transposing and/or broadening the peak energy delivery in the target tissue area and reducing the impact on non-targeted tissue. In another embodiment, a computer control unit may alter generated frequencies within a 100 MHz bandwidth of an initial frequency of 2.45 GHz (i.e., 2.4

Ghz to 2.5 Ghz). In yet another embodiment utilizing phase shifting or frequency sweeping, a computer control unit may shift the phase of the waveform of the microwave energy, once or several times, thereby transposing and/or broadening the peak energy delivery in the target tissue area and reducing the impact on non-targeted tissue. This phase shifting can minimize hot spots along the cable by reducing standing waves that may develop along the length of the cable due to non-uniformities in cable manufacturing and reflected power due to variable physiological properties, for example impedance mismatches caused by variable tissue dielectric properties. This leads to improved life and efficiency of the cable. In yet another embodiment utilizing phase and frequency sweeping, a computer control unit may both shift the phase and alter the frequency of the waveform of the microwave energy, once or several times, thereby transposing and/or broadening the peak energy delivery in the target tissue area and reducing the impact on non-targeted tissue. Frequency sweeping or phase shifting implemented during the procedure can be done to minimize reflected power not absorbed by the target tissue due to environmental factors, for example, tissue impedance.

The control unit may be configured to adaptably and adjustably modulate the emitted frequency, the phase, and the amplitude to provide optimum energy transfer to a target location in the artery wall and surrounding tissue to account for differences in absorption of the emitted energy from patient to patient while avoiding unintended or unwanted damage to the tissue receiving the emitted energy.

In one embodiment, the control unit may include a computer processor such as a central processing unit (CPU), memory, operating software stored in memory, and various input and output (I/O) devices or data paths. Memory can include any one or a combination of volatile memory elements (e.g., random access memory (RAM), such as DRAM, SRAM, SDRAM, etc.) and nonvolatile memory elements (e.g., EEPROM, FLASH, FRAM, ROM, hard drive, tape, CDROM, etc.). Memory may also include electronic, magnetic, optical, and/or other types of storage media. Memory can be distributed among various components remote from yet interconnected with one another, or can reside on a single component.

The software stored in memory may include one or more computer programs, each including executable instructions by the CPU. An operating system may control the execution of other computer programs and can provide scheduling, input-output control, file and data management, memory management, and communication control and related services. The software may allow for different operational modes. The operational modes may be preprogrammed into the control unit. A patient's physician can select a particular operational mode depending on patient characteristics, disease characteristics, and other variables. Patient characteristics that may be considered in selecting an operational mode include, but are not limited to whether the patient did not respond or had an inadequate response to previous renal denervation procedure; whether the patient did not respond or had an inadequate response to certain pharmaceutical treatment(s); imaging of a patient's targeted nerves and the corresponding radial depth from an adjacent artery or vein and/or a patient's targeted nerve based on nerve density; body-mass-index; the presence or absence of certain biomarkers, including, but not limited to, level of hypertension, muscle sympathetic nerve activity, norepinephrine concentration, aldosterone concentration, renin concentration, C-reactive protein levels, plasminogen activator inhibitor-1 levels, etc. and certain anatomical indications that may be present, for example, artery size, number of arteries, bifurcation position, artery calcification or stenosis, etc. Disease characteristics that may be considered in selecting an operational mode include, but are not limited to the severity of disease, for example, severity of hypertension; the presence or absence of hyperactive sympathetic activity, which can be identified by at least muscle sympathetic nerve activity and/or intravascular nerve activity, among others; and clinical data demonstrating or suggesting optimized treatment regimens. Other variables that may be considered in selecting an operational mode include, but are not limited to the physician's experience and equipment operating requirements.

In some embodiments, certain operational modes may be selected by the user or physician prior to emitting microwave energy from the emitter. The operational modes are preprogrammed settings that allow a user or physician to select a certain dose amount of microwave energy along with other parameters. In one embodiment, for example, operational modes that could be selected are "High", "Medium", and "Low". The "High" operational mode would contain software that delivers an increased amount of microwave energy compared to the "Medium" and "Low" operational modes. Each operational mode is associated with software controlling the different parameters described herein, including, but not limited to vessel wall temperature, tissue temperature inferred at some depth radial from the center of the vessel, power input, power output, cooling flow level, frequency, phase, power on time, power alteration rate, cooling flow volume/rate, time the microwave ablation apparatus dwells in vessel, and balloon inflation/deflation rates. In these embodiments, the user selects the operational mode through one or more knobs, keyboards, mouses, touch screens, PLCs, or any other user interfaces or input devices.

The I/O devices may include input devices, such as a keyboard, mouse, touch screen, PLC, and/or any other user interface. The I/O devices may also include output devices, such as a computer display, a modem, a router, serial and parallel wired and wireless communication components and any other elements needed to connect to, for example, another computer or device via a local network or the Internet whether wired or wirelessly. The I/O devices may further include any element or device in a feedback control system for controlling the operation and performance of the balloon catheter and associated system.

To help ensure a desired energy transfer to a target tissue and tissue depth, in an environment where the diameter of the artery may vary by a factor of three or more between patients, and where the blood and body chemistry within a patient and from patient to patient may significantly change the dielectric and conductivity characteristics of the treated tissue, the balloon catheter apparatus and associated system may include a control system. For example, the balloon catheter apparatus and associated system may be configured to measure the forward and reflected energy delivered to the cable and to the emitter.

The balloon catheter apparatus and associated system may also include a feedback signal originating at or near the emitter to permit the control unit to modulate or otherwise control the amount and/or frequency of electromagnetic energy emitted from the antenna. Low frequency signals derived from detectors configured for transmitted and reflected power measurement may be provided as control inputs to allow proper management of frequency and/or power output control signals from the control unit. Sensors to measure the real-time temperature at or near the emitter, the inside of the balloon, the wall of the balloon, or in the tissue may be included to provide the control unit with data sufficient to help modulate or adjust, in real-time, the frequency, phase, and amplitude of the emitted energy and/or flow rate of the dielectric agent. The balloon catheter apparatus and associated system may be configured so that the collection and transmission of temperature signals does not disturb the distribution of microwave energy from the emitter.

The balloon catheter apparatus and associated system may also include a feedback signal originating at or near the power amplifier, which may include a power amplifier output of catheter coaxial cable connection, to permit the user to modulate or otherwise control the amount and/or frequency of electromagnetic energy.

Sensors to measure electromagnetic field can be located on the distal end of the inflatable balloon catheter apparatus. The electromagnetic field measurements serve as an indicator of energy generated and, in turn, temperature of the surrounding environment, including, but not limited to, a targeted tissue, a non-targeted tissue, a vessel wall, and a balloon catheter apparatus.

Temperature feedback to the user may be employed in several embodiments of this invention, where such temperature feedback includes detection of temperature at the balloon end of the catheter at one or more locations, and such detection includes one or more detection devices. Several temperature detection devices are known in the art, and some examples of possibly suitable devices include fiber optic sensors, liquid crystal light capturing or colorimetric sensors, thermistors, resistance-temperature-detectors, semiconductor junction characteristic temperature sensors, microwave radiometer, acoustic reflectivity sensors, and numerous others. Of particular interest are non-conductive devices such as fiber optic and liquid crystal based, since the effect of microwave radiation on the sensor and the effect of the sensor and wiring on the emitter radiation pattern is minimized. It is also contemplated to incorporate very small and high resistance sensors of the conductive devices into the balloon catheter apparatus and associated system.

The sensors of the inflatable balloon catheter apparatus provide direct measurements. However, the control system can be configured to calculate, estimate, or infer data from those direct measurements. For example, temperature measurements from an arterial wall can be used to calculate, estimate, or infer temperature values for tissue at some radial depth from the arterial wall.

When radiometers are employed in the inflatable balloon catheter apparatus, the radiometers can be used to determine, along with the control system, energy delivered and/or heat generated at a specified radial depth. In some embodiments, one or more antennas function as the radiometer. In these embodiments, the antenna is configured to receive reflected radiation information from the target tissue zone and transmit the radiation information to the control system via a coaxial cable. The use and applicability of radiometric thermometry are further described in Wang et al., "Microwave Radiometric Thermometry and its Potential Applicability to Ablative Therapy" (Journal of Interventional Cardiac Electrophysiology, Vol. 4, pp. 295-300 (2000)) and U.S. Pat. No. 7,769,469 (Carr), which are hereby incorporated by reference in their entirety.

Pressure sensors internal to the balloon catheter apparatus and/or at the proximal end near the fluid pump may also be utilized to monitor and/or permit manual or automatic adjustments of the performance of the balloon catheter apparatus and associated system. For example, one or more sensors may be in communication with a computer system configured to monitor a pressure of fluid in the one or more coolant channels and adjust a flow rate and/or fluid volume output of the fluid pump.

These feedback control systems and associated sensors may be configured to allow the user to adjust the balloon catheter system in real time or programmed such that a control unit will make operational decisions (e.g., stop all energy delivery) when the feedback signals report the status of certain elements in the balloon catheter apparatus and associated system.

For ensuring patient safety, the balloon catheter apparatus and associated system may include both a primary and a secondary control system to safely shut down the system in the event of an unanticipated fault or improper behavior of system software or hardware.

To operate the balloon catheter apparatus and associated system, electrical power may be obtained from a source that is suitable and approved for use with medical equipment in connection with interventional techniques for treating disease. In one embodiment, electrical power is obtained by one or more electrical outlets. In another embodiment, electrical power is obtained through a battery power supply. In another embodiment, electrical power is obtained by a backup power supply system to minimize disruptions of an in-process treatment on a patient in the event of loss of the primary source of electrical power. In one embodiment, the backup power supply system includes a battery. In another embodiment, the backup power supply system includes a primary battery and a backup battery.

During use, the balloon catheter apparatus and associated system may monitor and/or adjust one or more operating parameters associated with the delivery of electromagnetic energy to a patient. For example, to monitor and/or adjust one or more operating parameters, the balloon catheter apparatus and associated system may include one or more temperature sensors, one or more fluid flow sensors, one or more timers, one or more electrical power consumption meters, one or more voltage sensors, one or more current sensors, one or more pressure transducers, and any other sensor or measurement device to measure and/or report measurement data to one or more CPU's configured to perform one or more computer algorithms according to one or more predefined rules. The one or more predefined rules may include predefined operating ranges for each parameter being monitored or measured. Such operating ranges can be preprogrammed and stored in memory. The one or more CPU's may be housed in a housing electrically connected to the balloon catheter. The balloon catheter apparatus and associated system may be configured to transmit data to a remote computer. The balloon catheter apparatus and associated system may be configured to receive data from a remote computer via a wired link such as RS232, CAN bus, Ethernet, Firewire, USB or a wireless link such as Bluetooth, Zigbee, 802.11a/b/c/n.

In one embodiment, one or more aspects of the balloon catheter apparatus and associated system may monitor the amount of energy provided by the emitter to the patient's arterial walls. If, for example, should detected temperature be outside a desired temperature range or limit, the system will initiate a fail-safe mode to cease or reduce delivery of microwave energy to tissue. For example, if the balloon catheter apparatus and associated system is operating at 100 percent duty cycle and/or at 100 percent microwave power amplifier output level, and the system determines that the measured temperature falls outside of a predetermined temperature range or limit, a control algorithm may reduce the duty cycle for microwave power delivery and/or reduce the microwave power amplifier output level to a value that is less than 100 percent to reduce the temperature to be within desired limits.

Treatment of a disease with the balloon catheter and associated system requires bringing the target tissue adjacent to the artery to an appropriate temperature range or band, then maintaining that temperature for an appropriate period of time. To do this, the control unit may be configured to provide a predetermined, nominal energy delivery at a rate sufficient to bring the target tissue up to the desired temperature range or band in a reasonable time, then using one or more feedback control system, or predetermined energy levels which correlate to resulting temperature levels provide for the delivery of energy to maintain the temperature in a desired temperature band or range for a desired period of time. In preferred embodiments, the target tissue will be heated to at least 40° C. In other preferred embodiments, the target tissue will be heated up to a range of 40° C. to 100° C. In other preferred embodiments, the target tissue will be heated to a range of 40° C. to 60° C. In other preferred embodiments, the target tissue will be heated to a range of 48° C. to 75° C. In preferred embodiments, the energy application cycle will be at least 15 seconds. In other preferred embodiments, the energy application cycle will range between 15 seconds to 600 seconds. One or more pulses of energy may be applied per application cycle. In other embodiments, a wall temperature of 46° C. to 50° C. as measured or inferred at the inner diameter of the vessel may be coupled with an application cycle of 120 to 180 seconds. The balloon catheter apparatus and associated system is designed to optimize therapy by varying the energy application cycle and target tissue temperature. One of ordinary skill would appreciate that the optimal dose for a given patient may require manipulations of the balloon catheter apparatus and associated system as described herein after monitoring vessel wall temperature and target tissue temperature. Achieving the optimal dose for a given may be accomplished through manipulation of power input, power output, cooling flow rate, coolant temperature, frequency, phase, power on time, power alternative rate, cooling flow volume or rate, balloon catheter apparatus dwell time, balloon inflation/deflation rate, among others.

Turning now to the figures, wherein like reference numerals refer to like elements, there is shown one or more embodiments of a balloon catheter and associated system to emit microwave energy to excite and thermally disrupt or ablate one or more sympathetic nerves. Thermal disruption or ablation of one or more sympathetic nerves would have therapeutic benefits for patients suffering from Cardiovascular Hypertension, Insulin Resistance, Diabetes, Diabetic Nephropathy, Chronic Kidney Disease, Congestive Heart Failure, Hepatorenal Syndrome, End-Stage Renal Disease, Atrial Fibrillation, Ventricular Tachycardia, Pulmonary Hypertension, COPD, and Acute Renal Disease. Although the figures and the instant disclosure describe one or more embodiments of a balloon catheter and associated system, and in particular, of a microwave delivery system, one of ordinary skill in the art would appreciate that the teachings of the instant disclosure would not be limited to these embodiments. In particular, one of ordinary skill would appreciate that each of the embodiments of the disclosed balloon catheter and associated system has applicability to any number of fields or applications, including most any situation involving requiring the ablation or thermal damage to tissue or nerves.

FIG. 1 shows an exemplary balloon catheter apparatus comprising modular catheter 20 removably connectable to steerable catheter handle 30, a guide wire port 50, ports for fluid or gas introduction 60, an inflatable balloon 40 housing a microwave emitter, which is associated with a system comprising a power source 80, and a control unit 70 which includes an RF generator, and display. Collectively, these aspects represent the balloon catheter apparatus and associated system 10. The steerable catheter handle 30 is connected to a guide wire port 50. A guide wire can be removably inserted into the shaft of the catheter 20 from the guide wire port 50 and used to advance the balloon catheter apparatus through the vasculature. The steerable catheter handle 30 is also connected to an inflation port 60 used to inflate the balloon 40 with fluid or gas. The steerable catheter handle 30 is further connected to a control unit 70, which includes a display and a RF generator. The display, such as a touch screen display, comprises a user interface for user data entry or commands to, for example, calibrate or otherwise operate the balloon catheter and associated system 10. The control unit 70 may include connections to user interface, power conversion circuitry for converting input power from alternating current to direct current and vice versa, and sensing circuitry and software for monitoring sensors, interpreting data received from sensors, and for adjusting the signal delivered to emitter 41. The control unit 70 may be configured to execute computer executable instructions to perform the functions described above, including phase sweeping. The control unit 70 is connected to a power source 80, which may include alternating current line power provided by an electrical utility provider (i.e., 120 volt, 60 Hz in the U.S.) or power provided by a portable battery or fuel cell system. The balloon catheter apparatus is designed to be introduced into the patient's body whereas the associated system will remain outside the patient's body.

Upon completion of a desired exposure or dose of energy to a target tissue in an artery, control unit 70 causes delivery of such energy to cease. Catheter 20 and balloon 40 may then be maneuvered as needed for additional dosing of the same or opposite artery, or extracted from the patient's body.

Balloon catheter apparatus and associated system 10 is configured to be sterilized before use on a patient. Acceptable methods for disinfection of the various components of balloon catheter apparatus and associated system 10 include sterilizing for required duration at a required temperatures, concentrations, and pH's.

Following post-sterilization and prior to use of balloon catheter and associated system 10 in a therapeutic procedure, a series of computerized self-tests may be conducted to determine any component or parameter faults and to verify that all aspects of control unit 70 and associated sensing system are functioning properly. Upon completion of these self-tests, the catheter and balloon assembly may be connected to control unit 70 and tested while still bagged to retain cleanliness. The self-test sensor assembly may allow calibration of the components of sensing system with control unit 70.

Balloon catheter apparatus and associated system 10 may be configured to continuously or at discrete intervals monitor input data or otherwise check for component or parameter faults whenever the system is powered on or during use. Diagnostic data from the self-tests and data including sensor data and operational or performance data acquired during operation or use of balloon catheter apparatus and associated system 10 may be stored in memory for subsequent download, wired or wirelessly, to a computer for tracking the performance of any particular balloon catheter apparatus and associated system 10 against other balloon catheters and associated systems 10's. Alternatively, such data may be wired or wirelessly transmitted or otherwise uploaded or downloaded to a computer in real-time. The computer may be a remote computer or device including a computer server. Balloon catheter apparatus and associated system 10 may be configured to automatically shut down or otherwise cease generating or emitting electromagnetic radiation on occurrence of a fault. When shutting down, a designated plurality of acquired data and operational settings of balloon catheter and associated system 10 may be saved in non-volatile memory in balloon catheter apparatus and associated system 10.

Calibration checking and configuration of the balloon catheter apparatus and associated system 10 is completed in the operating room to verify prior calibration of the balloon catheter apparatus and associated system 10 in lab conditions and to ensure the balloon catheter apparatus and associated system 10 is properly configured for the specific patient and procedure.

Following staging of balloon catheter apparatus and associated system 10 and its various hardware components in proximity to the patient, balloon 40 and catheter 20 may be introduced into the patient's femoral artery, radial artery, or other vascular access point. As will be appreciated by those of skill in the art, the composition of the catheter must be flexible enough to advance the catheter to the desired position within the patient's vasculature and rigid enough as to avoid unwanted folding when the catheter is advanced through the patient's vasculature. In some embodiments, the catheter may be composed of materials of different rigidity. For example, a flexible higher loss coaxial cable on the distal half or portion of the catheter may be joined to a low loss rigid coaxial cable on the proximal half or portion of the catheter. The flexible cable portion may comprise a braided metal outer cover whereas the more rigid proximal portion may comprise a copper outer cover. A further example includes a flexible catheter sheath on the distal half of the catheter joined to a rigid catheter shaft on the proximal half of the catheter. A rigid distal portion allows for easier catheter positioning while a flexible distal portion allows for increase maneuverability of the distal portion of the catheter housing the emitter. The catheter 20 will be traversed over a guide wire 92. In preferred embodiments, the guide wire 92 will have an outside diameter of 0.014, 0.018, or 0.035 inches. In preferred embodiments, the catheter or sheath will have an outside diameter ranging from 4 French to 9 French. Catheter 20 may be manipulated by the user using catheter handle 30 to advance balloon 40 in artery at a desired longitudinal location for delivery of microwave energy to targeted tissue 106. A fluoroscope imaging system may be useful toward determining the longitudinal position of balloon 40 in the artery. Once positioned, the user may, manually or through the control system, inflate balloon 40 with fluid through the inflation port 60 to secure catheter 20 and balloon 40 positions within the artery and to prepare balloon 40 for receipt of externally supplied cooling fluids, if needed, or to enhance blood flow therethrough via lumen or surface cooling channels.

A dose of microwave energy may then be commanded by control unit 70 to be emitted from emitter 41. Control unit 70 generates a microwave signal and transmits the signal to emitter 41 via cable 90. In one embodiment, an emitter 41 emits a volumetric field of microwave energy 360° approximately symmetrically about a longitudinal axis to excite tissue at or near the renal nerves located approximately 0.5 millimeter to approximately 12.0 millimeter radially outward from the inner wall diameter surface of renal artery. In another embodiment, an emitter 41 emits a volumetric field of microwave energy 360° approximately symmetrically about a longitudinal axis to excite tissue at or near the renal nerves located approximately 0.5 millimeter to approximately 12.0 millimeter radially outward from the inner wall diameter surface of the aorta.

In one embodiment, an emitter 41 emits a volumetric field of microwave energy in a focused direction to excite tissue at or near renal nerves located approximately 0.5 millimeter to approximately 12.0 millimeter radially outward from the inner wall diameter surface of renal artery. In another embodiment, the dose is provided in a plurality of 15 to 600 second pulses. The duration of the pulses may be varied by the user if desired for a particular patient or procedure. The pulses can occur in a single spot or multiple longitudinal locations within either one or both renal arteries. In still another embodiment, the energy dose is provided in a single transmission while the emitter is either stationary or being advanced in a linear longitudinal pattern or a spiral longitudinal pattern. As described above, various aspects of the applied dosage may be varied according to patient anatomy or other needs. For example, the applied frequency, frequency sweep parameters, waveform amplitude, power output, dosage dwell time, and dielectric agent flow rate may be varied by control unit 70 while taking into account real-time data input from temperature sensors, pressure sensors, and the like or from user input parameters predetermined regarding patient anatomy. Frequency data including the applied frequency and waveform, frequency sweep data including frequency range and generated waveform, dosage dwell time, sensor data including temperature, pressure and fluid flow data, performance limit data and/or user selected setting data including maximum and minimum temperature, pressure, flow rate, dosage dwell time, or any other setting or data may be displayed in a computer display or user interface, including a display or user interface remote but wired or wirelessly connected to balloon catheter apparatus and associated system 10.

Balloon catheter apparatus and associated system 10 may be configured to continuously or at discrete intervals monitor input data or otherwise check for component or parameter faults whenever the system is powered on or during use. Diagnostic data from the self-tests and dating operation or use of balloon catheter apparatus and associated system 10 may be stored in memory for subsequent download, wired or wirelessly, to a computer for tracking the performance of any particular balloon catheter apparatus and associated system 10 against other balloon catheter apparatuses and associated systems 10's. Alternatively, such data may be wired or wirelessly transmitted or otherwise uploaded or downloaded to a computer in real-time. The computer may be a remote computer including a computer server or a handheld device.

In one application of the balloon catheter apparatus and system 10, upon completion of the microwave disruption of nerves in one renal artery, the process may be duplicated in the opposite renal artery by repositioning balloon 40 accordingly. Upon completion of the renal denervation procedure, catheter 20 and balloon 40 may be retracted from the patient's body and balloon catheter apparatus and associated system 10 may be powered down.

Figure 2:
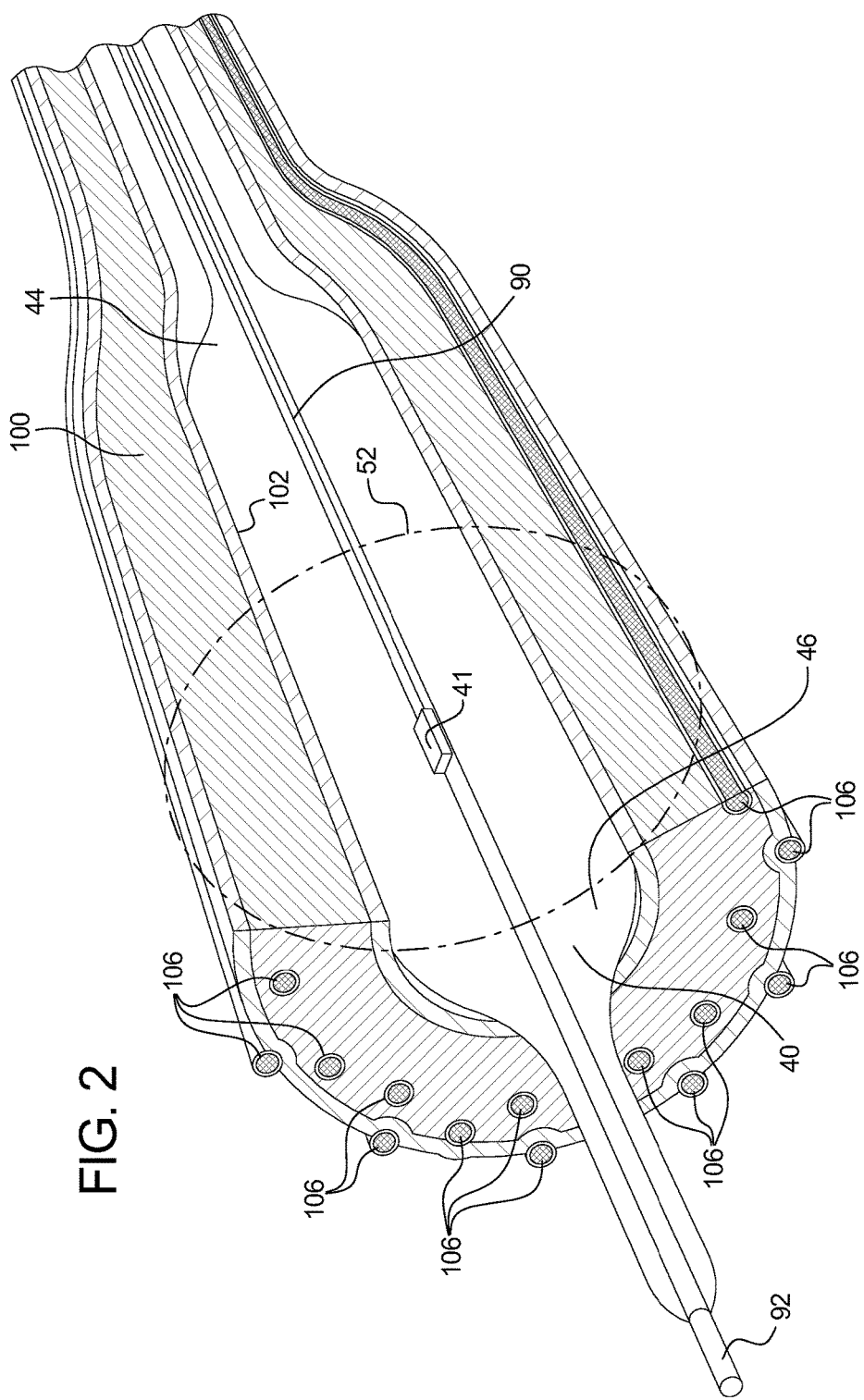
FIG. 2 is a perspective, cross-sectional view of the distal end of one embodiment of a balloon catheter apparatus and associated system.

FIG. 2 depicts the distal end of a balloon catheter and associated system 10 designed to be partially introduced into the patient's body. As shown in FIG. 2, emitter 41 comprising microwave antenna 43 is positioned inside balloon 40 and is configured to radiate electromagnetic microwave radio frequency energy 360° about the centerline of an artery as described above. In one embodiment, the electromagnetic energy is emitted in the shape of discus 52, where the hub of discus 52 is thicker than at the periphery of discus 52. Advancing the balloon and catheter with the assistance of the guide wire 92 through the vasculature, the user will inflate the balloon 40 within artery once the emitter 41 and balloon 40 are properly oriented adjacent the target tissue 106. The target tissue 106 in this figure represents nerves. As described above, the emitted electromagnetic energy raises the temperature of target tissue located at a desired radial distance from emitter 41 as describe above to a predetermined or desired ablation or denervation temperature over a predetermined or desired period of time. FIG. 2 also shows a cable 90 for passing signals to and from emitter 41. Cable 90 could also connect a sensing system comprising a plurality of temperature and pressure sensors for sensing, among others, energy delivery, temperature and pressure to control unit 70 for generating and amplifying a signal to enable emitter 41 to emit desired electromagnetic waves and for monitoring the delivery of radio frequencies from emitter 41 to tissue surrounding balloon 40. One of ordinary skill would appreciate that cable 90 may include a coaxial cable.

Cable 90 is connected to control unit 70 and extends therefrom to emitter 41. In some embodiments, the cable 90 may be affixed to the catheter 20. In further embodiments, the cable 90 may be attached to a catheter handle 30 and/or the control unit 70 which is attached to the proximal end of the balloon catheter. Cable 90, which has a smaller diameter and is more flexible than catheter 20, may lie inside catheter 20 and is configured to extend into the patient's body to emitter 41. Catheter 20 and cable 90 may optionally be contained within a sheath, a hypotube, or a multi-lumen catheter. Catheter 20 is configured as a conduit for wiring, including cable 90, to and from control unit 70 for communicating a signal to emitter 41 for radiating electromagnetic wave energy to excite body tissue receiving the emitted electromagnetic waves, and for communicating a signal from emitter 41 comprising, for example, an amount of power emitted from emitter 41. Catheter 20 is configured as a conduit for wiring connecting the control unit 70 to any sensors positioned in or around balloon 40. Catheter 20 is also configured as a conduit for communicating any externally supplied cooling fluids to balloon 40. Catheter 20 is additionally configured to communicate or provide hydraulic pressure to inflate balloon 40 by transferring fluid to the balloon from an inflation port 60 on the outside of the body near the proximal end of the catheter. Those skilled in the art will appreciate that fluid can be used to inflate the balloon 40 via the inflation port 60 and would be familiar with methods of inflating the balloon with fluid. Those skilled in the art will appreciate that a sufficient amount of pressure is required to stabilize the balloon within the artery. The system should not mechanically stretch the vascular walls, which would cause unwanted damage.

The inflation port 60 may also be configured to deliver cooling fluid to the channels within the interior walls of the balloon such that an untargeted tissue, e.g., an artery wall, is cooled without the cooling fluid contacting the emitter 41. The inflation port 60 may also be configured to deliver cooling fluid to both the lumen of the balloon as well as the cooling channels to optimize the adjacent cooling of untargeted tissue.

Figure 3:
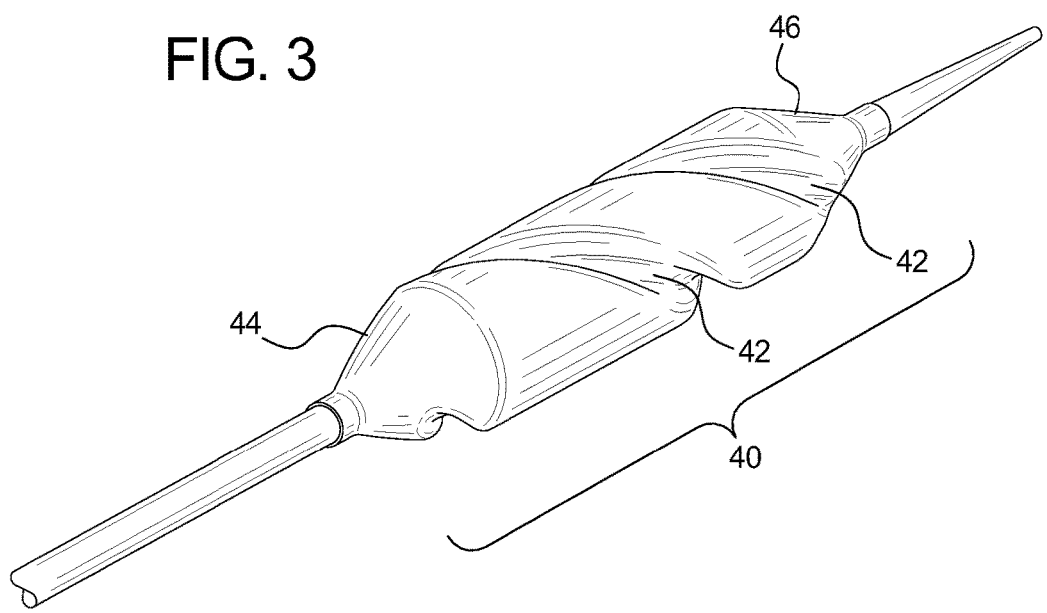
FIG. 3 illustrates a perspective view of one embodiment of an inflatable balloon of the balloon catheter apparatus in accordance with the disclosure herein.

As described above, balloon 40 may be configured to permit cooling fluids to flow through or past balloon 40 to regulate the temperature of any energy source, including emitter 41, and the temperature of inner wall 102 of an artery. In one embodiment, as shown in FIGS. 3-5, balloon 40 includes cooling channels 42. Cooling channels 42 may comprise spirally shaped channels formed in the outer periphery of balloon 40 for passing blood, which serves as a heat transfer means to draw heat away from the irradiated target tissue, effectively protecting untargeted tissue from thermal damage. In other embodiments, cooling channels 42 may comprise a lumen of balloon 40 from at least proximal end 44 to distal end 46 of balloon 40. In other embodiments, cooling channels 42 may comprise a lumen extending from the proximal end of the balloon catheter apparatus (located ex vivo when the balloon catheter is in place) through the distal tip of the balloon catheter apparatus. These cooling channels 42 may be configured to allow a dielectric agent to cool the balloon catheter apparatus, the emitter 41, the balloon wall, the untargeted tissue, or a combination thereof. The path the cooling channels 42 form will be dependent on what cooling is desired. If it is desired that the emitter 41 be cooled, the dielectric agent delivered by the cooling channels contacts the emitter or is in close proximity to the emitter 41 to effectively cool the emitter 41. If it is desired that the untargeted tissue be cooled, the dielectric agent delivered by the cooling channels contacts the untargeted tissue through an irrigation port or is in close proximity to the untargeted tissue through cooling channels within the balloon and/or balloon wall. In some embodiments, the balloon catheter apparatus contains only one cooling channel 42.

Figure 6:
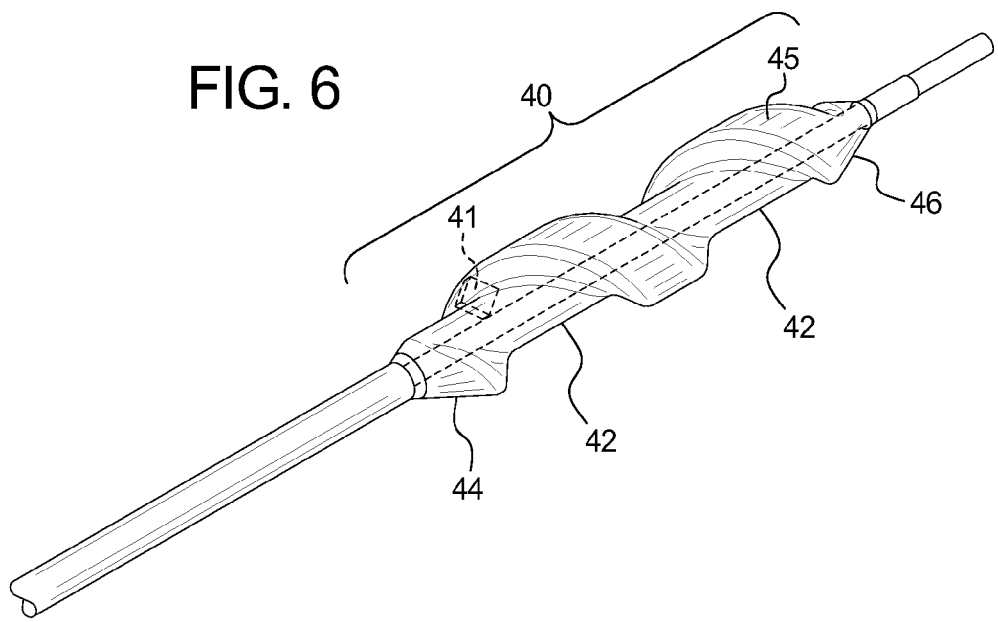
FIG. 6 illustrates a perspective view of another embodiment of an inflatable balloon of the balloon catheter apparatus in accordance with the disclosure herein showing a first position of an emitter.
Figure 7:
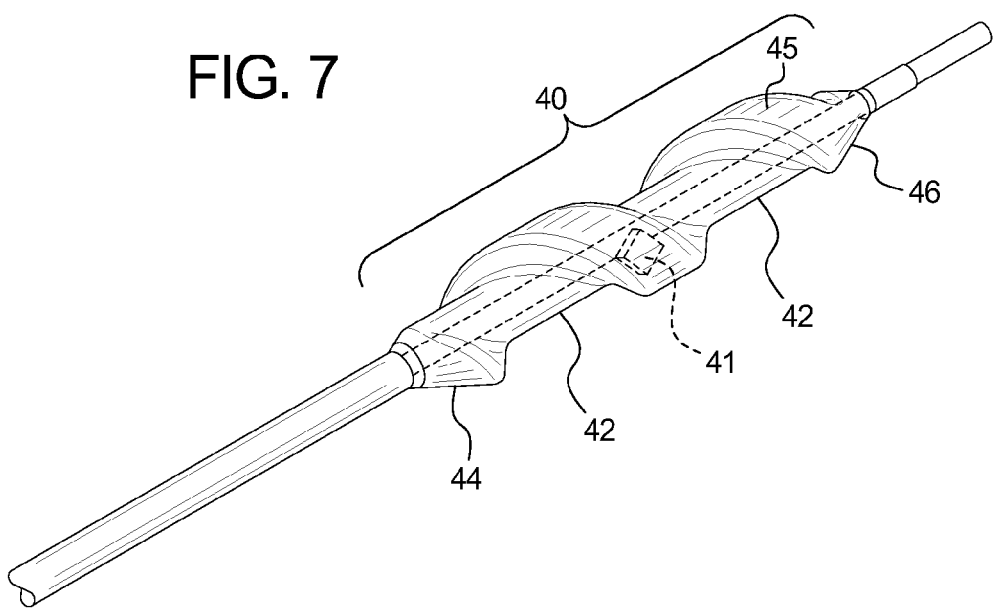
FIG. 7 illustrates a perspective view of the inflatable balloon of the balloon catheter apparatus shown in FIG. 6 showing a second position of the emitter of an inflatable balloon design.

FIGS. 6-7 depict another embodiment of inflatable balloon 40. The balloon catheter apparatus may contain an emitter 41 that is housed in the lumen of the catheter, proximal to the balloon 40, when advanced through the patient's vasculature. When the balloon catheter apparatus reaches its desired location, the user can then release the emitter 41 from the shaft of the catheter. The emitter 41 is guided from the proximal end 44 of the balloon 40 towards the distal 46 end of the balloon 40 along emitter channels 45. The emitter channels 45 may be formed within the surface of the balloon 40 or other material or aspect disposed within the balloon. The emitter channels 45 enable the emitter to travel in a linear or spiral path. The emitter 41 may travel from the proximal end 44 of the balloon 40 to the distal end 46 of the balloon 40 and, optionally, back from the distal end 46 of the balloon 40 to the proximal end 44 of the balloon 40 one or more times. FIG. 6 shows the emitter 41 beginning its path from the proximal end 44 of the balloon 40 along a spiral emitter channel 45. FIG. 7 illustrates the emitter 41 further advanced along a spiral emitter channel 45, relative to FIG. 6, from the proximal end 44 of the balloon 40 towards the distal end 46 of the balloon 40.

Figure 8:
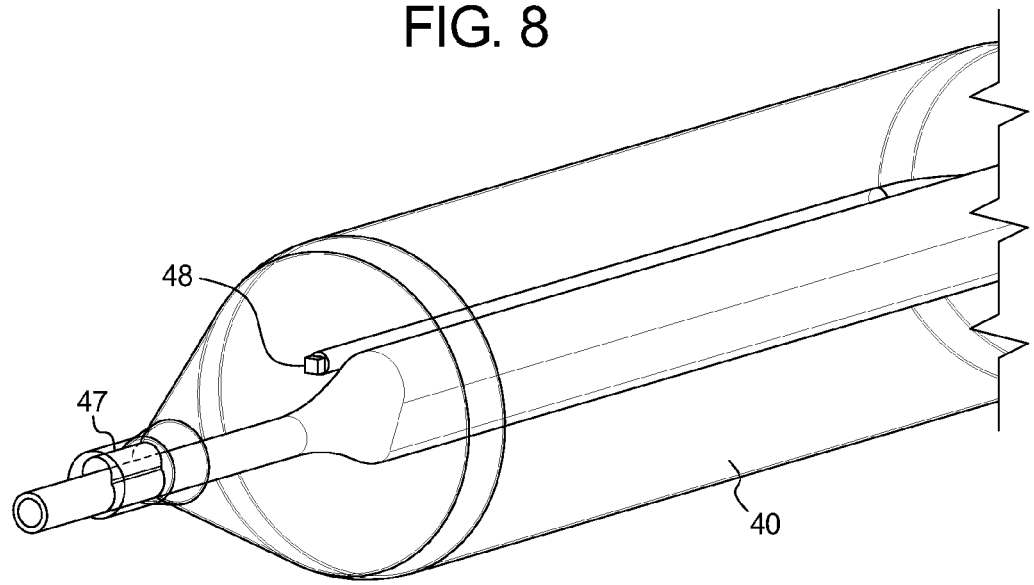
FIG. 8 illustrates an embodiment of the distal end of the inflatable balloon of a balloon catheter apparatus depicting one configuration of irrigation ports.
Figure 9:
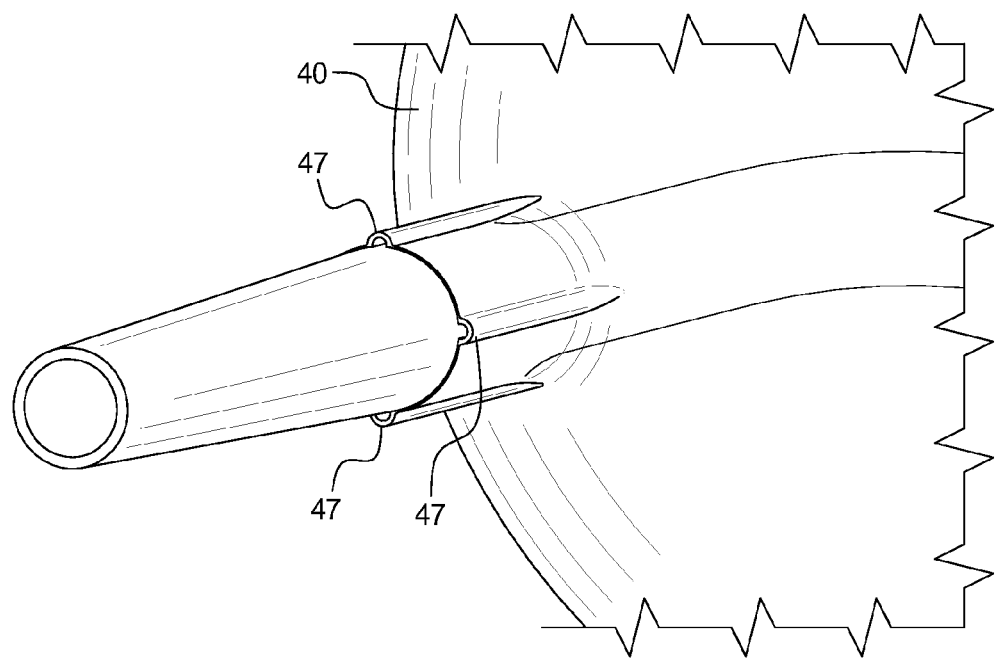
FIG. 9 illustrates a perspective view of an embodiment of the distal end of the inflatable balloon of a balloon catheter apparatus shown in FIG. 10 depicting another configuration of irrigation ports.
Figure 10:
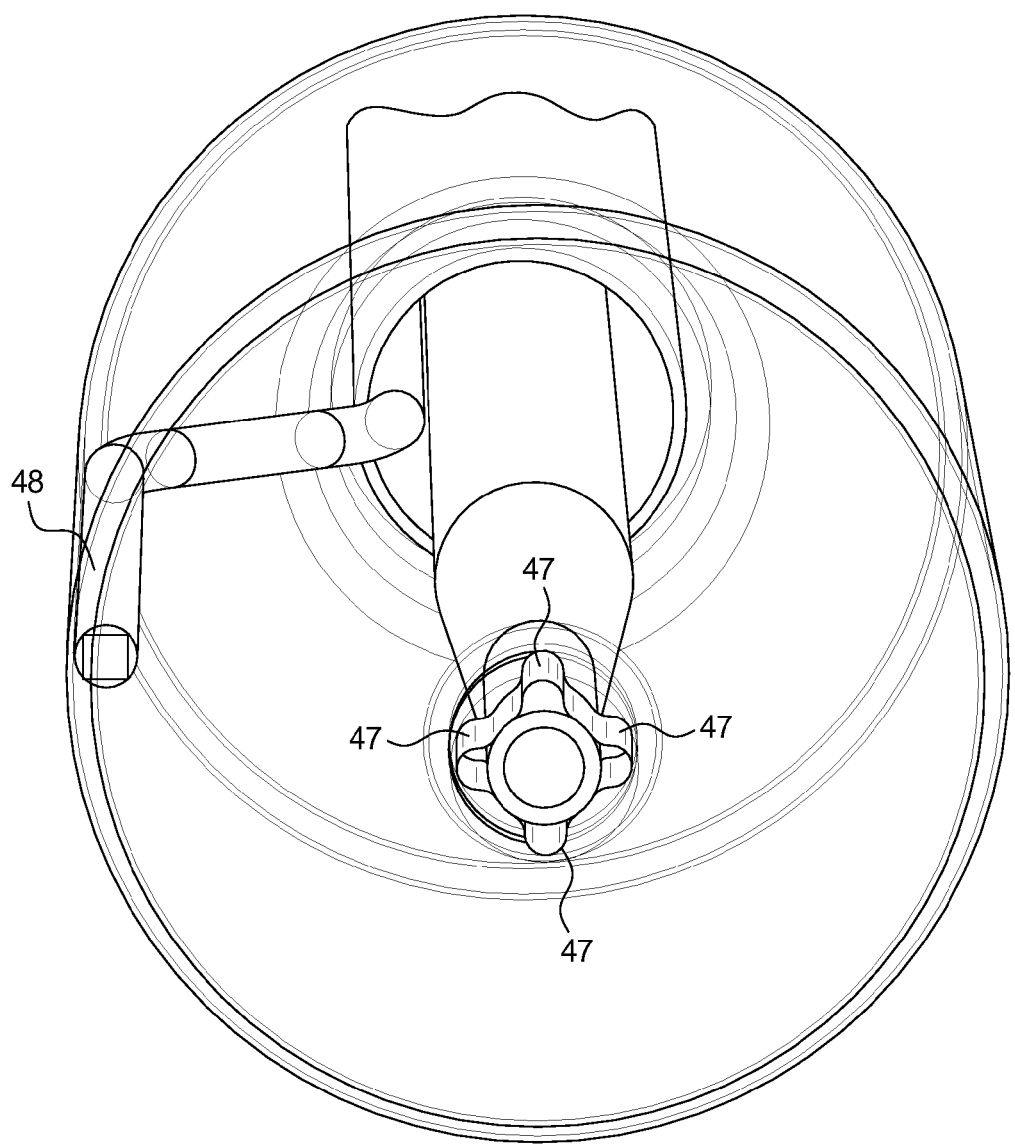
FIG. 10 illustrates an embodiment of the distal end of the inflatable balloon of a balloon catheter apparatus depicting the same orientation of irrigation ports as shown in FIG. 9.
Figure 11:
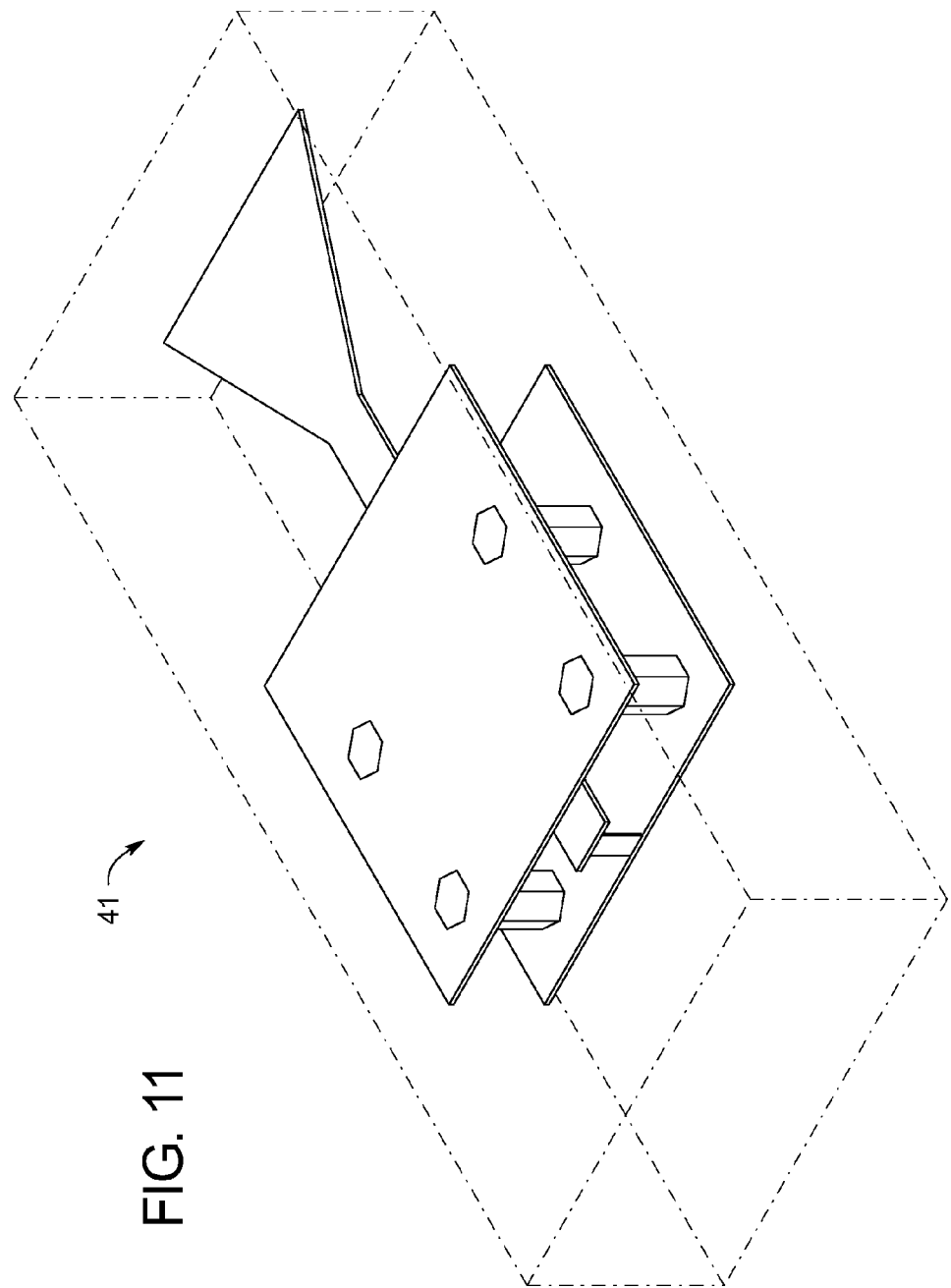
FIG. 11 illustrates an embodiment of an emitter in accordance with the disclosure herein.

FIGS. 8-10 show alternate embodiments of cooling channels terminating at one or more irrigation ports. FIG. 8 depicts an example of an irrigation port 47 located at the junction between the inflatable balloon 40 and the distal tip of the balloon catheter apparatus. The irrigation port 47 provides an access for fluid to flow out of the balloon catheter apparatus directly into a patient's vasculature. FIG. 8 also illustrates an embodiment of a monitoring sensor 48 of the present disclosure. The monitoring sensor 48 can include, but is not limited to, a temperature sensor, a pressure sensor, microwave radiometer, acoustic reflectivity sensors. The monitoring sensor 48 can be located inside the balloon wall as depicted, on the outside of the balloon wall, or integral within the balloon wall. The position of the monitoring sensor 48 relative to the emitter will dictate acceptable operational parameters for the control system. The monitoring sensor 48 is in communication with the control system of the balloon catheter apparatus. FIGS. 9 and 10 depict alternate views of an example of four irrigation ports 47 located at the junction between the inflatable balloon and the distal tip of the balloon catheter apparatus. The size, shape, and position of the irrigation port(s) 47 are dictated by the desired flow through the irrigation port(s) 47, which can be monitored by pressure sensors within the balloon catheter apparatus. FIG. 10 also depicts a monitoring sensor 48 of the present disclosure. In FIGS. 8-10 the irrigation port or ports is in communication with one or more cooling channels 42.

Figure 12:
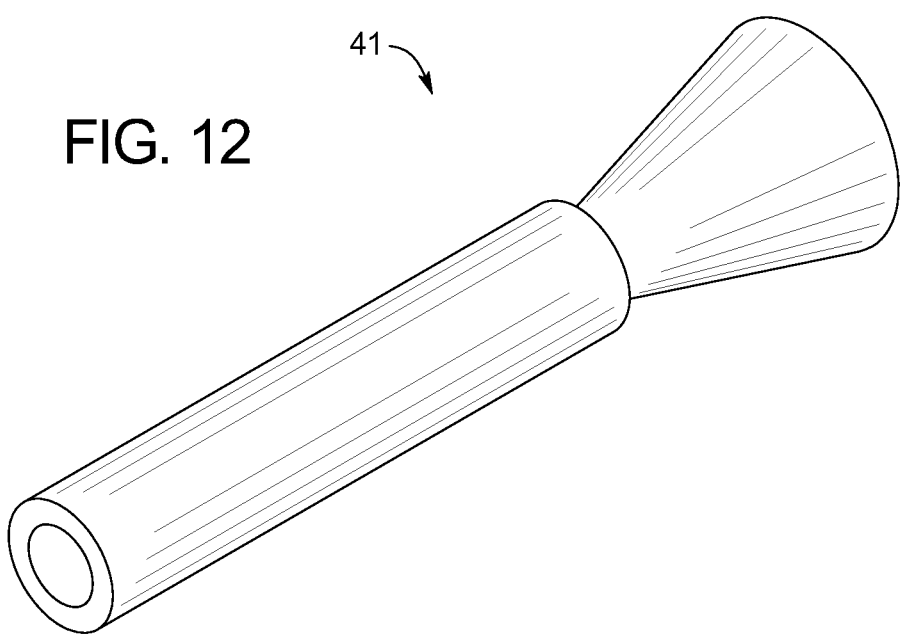
FIG. 12 illustrates an embodiment of an emitter in accordance with the disclosure herein.
Figure 13:
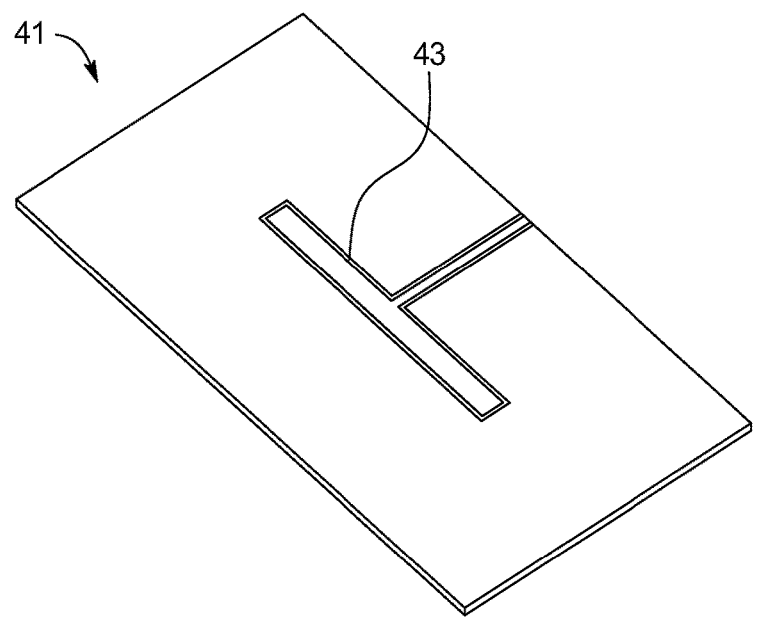
FIG. 13 illustrates an embodiment of an emitter in accordance with the disclosure herein.
Figure 14:
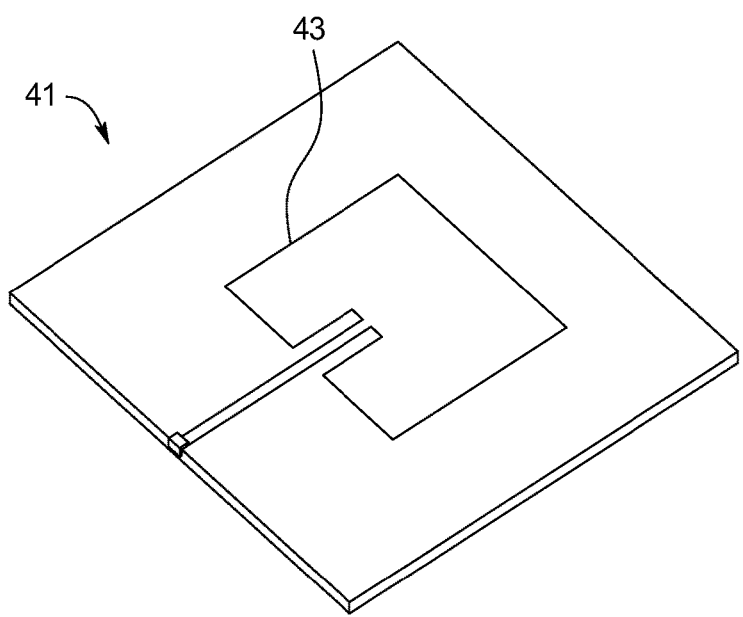
FIG. 14 illustrates another embodiment of an emitter in accordance with the disclosure herein.
Figure 15:
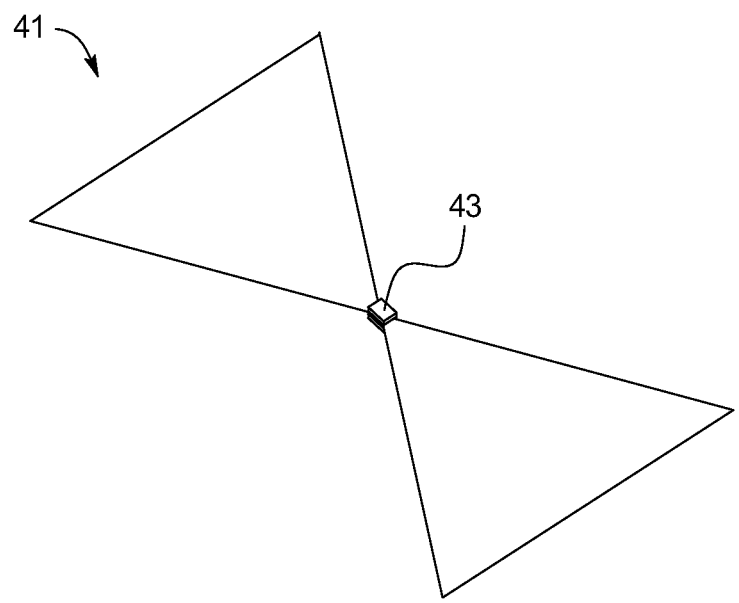
FIG. 15 illustrates another embodiment of an emitter in accordance with the disclosure herein.
Figure 16:
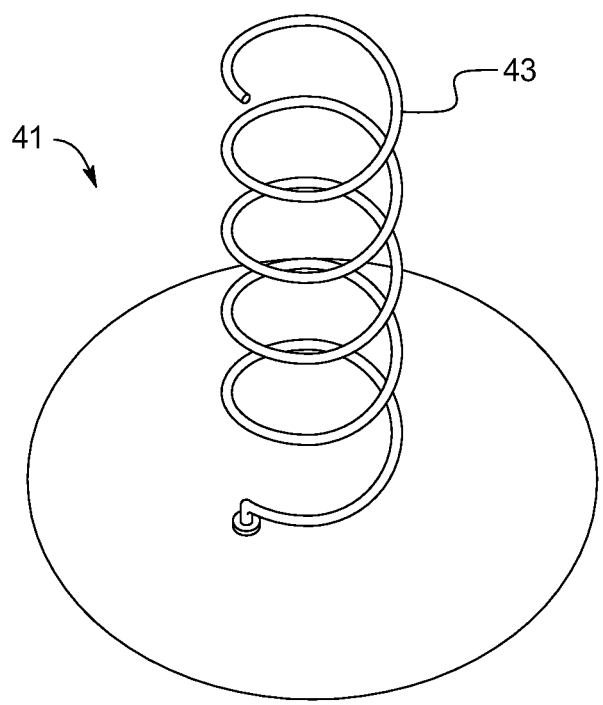
FIG. 16 illustrates another embodiment of an emitter in accordance with the disclosure herein.
Figure 17:
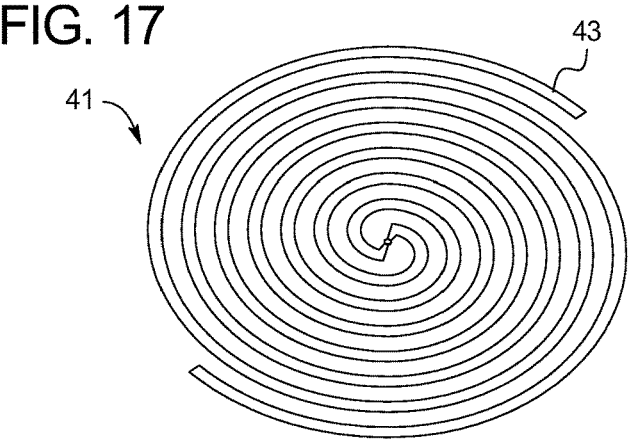
FIG. 17 illustrates another embodiment of an emitter in accordance with the disclosure herein.
Figure 18:
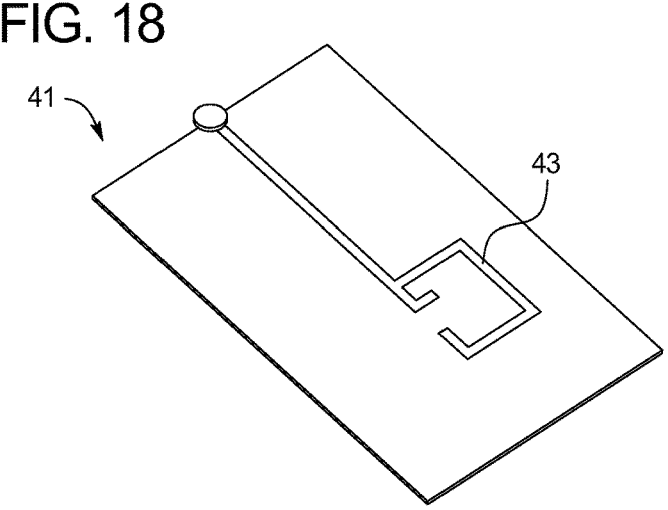
FIG. 18 illustrates another embodiment of an emitter in accordance with the disclosure herein.
Figure 19:
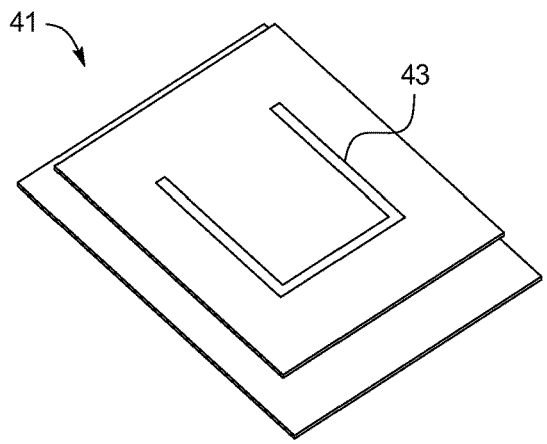
FIG. 19 illustrates another embodiment of an emitter in accordance with the disclosure herein.

FIGS. 11-19 show several alternate embodiments for emitter 41. As described above, the emitter can be an antenna 43 or a plurality of antennas. An antenna 43 can be formed in the shape or geometry as shown in FIGS. 11-19. The optimal antenna design will enable the balloon catheter apparatus and associated system to deliver microwave energy in a desired orientation and to a targeted tissue of a specific depth. For example, FIG. 12 depicts an exemplary conical antenna configuration; FIG. 13 depicts an exemplary dipole antenna configuration; FIG. 14 depicts an exemplary patch antenna; FIG. 15 depicts an exemplary bow-tie antenna configuration; FIG. 16 depicts an exemplary helical coil antenna configuration; FIG. 17 depicts an exemplary planar antenna configuration; FIG. 18 depicts an exemplary monopole antenna configuration; and FIG. 19 depicts an exemplary slot antenna configuration. One skilled in the art would appreciate that modifications of the antenna designs depicted in FIGS. 11-19 may be necessary to achieve the desired energy delivery in the desired orientation and to the target depths described herein.

Figure 20:
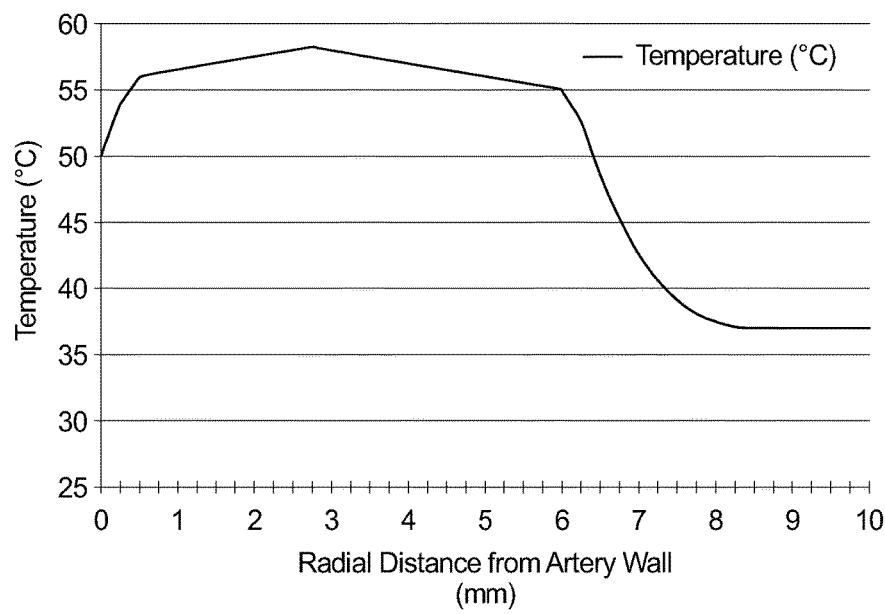
FIG. 20 illustrates a representative thermal gradient map resulting from microwave emissions applied to tissue from an emitter associated with one embodiment of a balloon catheter apparatus and associated system.
Figure 21:
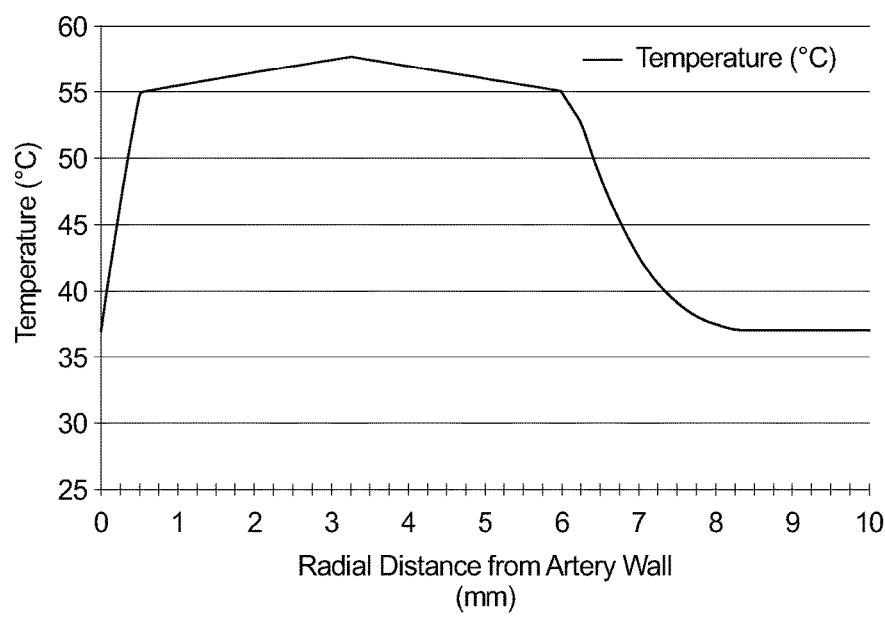
FIG. 21 illustrates a representative thermal gradient map resulting from microwave emissions applied to tissue from the emitter associated with the embodiment of FIG. 17 in combination with a cooling mechanism.
Figure 22:
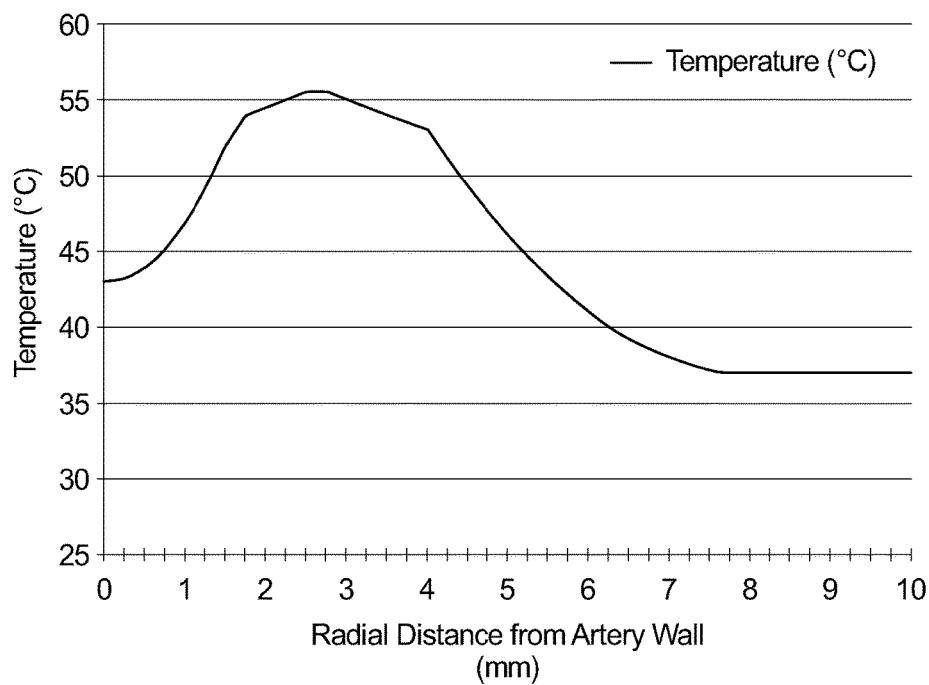
FIG. 22 illustrates a representative thermal gradient map resulting from microwave emissions applied to tissue from an emitter associated with another embodiment of a balloon catheter apparatus and associated system.
Figure 23:
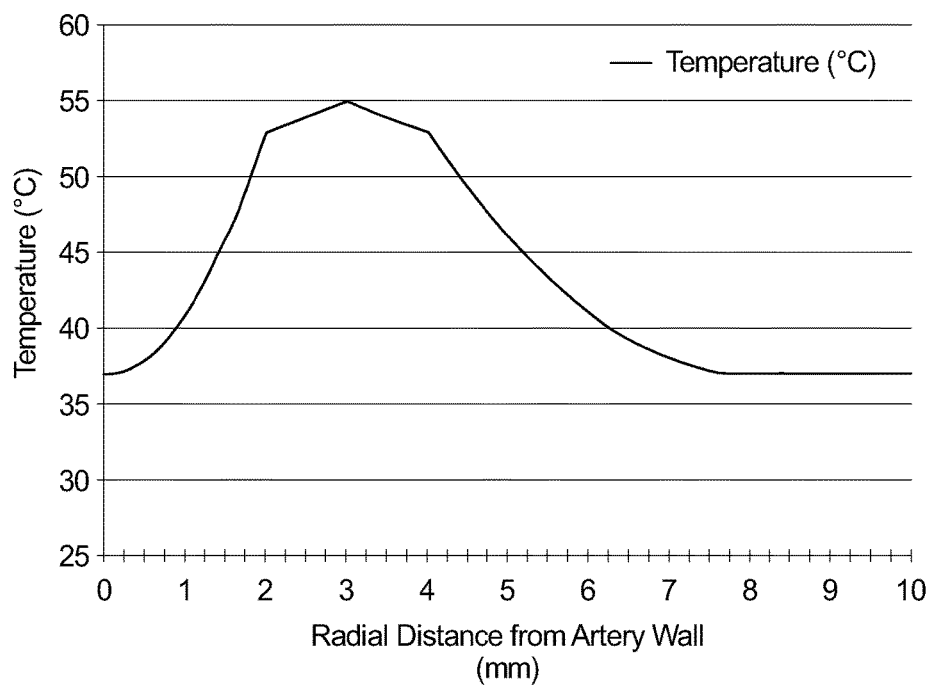
FIG. 23 illustrates a thermal gradient map resulting from microwave emissions applied to tissue from the emitter associated with the embodiment of FIG. 19 in combination with a cooling mechanism.

FIGS. 20-23 illustrate examples of the effect the operation of the balloon catheter apparatus and associated system 10 may have on adjacent tissue when the emitter is operational and emitting microwave energy. FIGS. 20-23 depict temperature gradients at an isolated timepoint after the emitter has been emitting microwave energy for a given time. FIG. 20 depicts an example of the effect the balloon catheter apparatus and associated system 10 may have on adjacent tissue when the balloon catheter apparatus and associated system 10 is targeting tissue at a radial depth of 0.5 mm to 6.0 mm from the inner surface of an arterial wall while the various cooling and heat transfer mechanisms described herein are not employed. FIG. 21 depicts an example of the effect the balloon catheter apparatus and associated system 10 may have on adjacent tissue when the balloon catheter apparatus and associated system 10 is targeting tissue at a radial depth of 0.5 mm to 6.0 mm from the inner surface of an arterial wall while the various cooling and heat transfer mechanisms described herein are employed. FIG. 22 depicts an example of the effect the balloon catheter apparatus and associated system 10 may have on adjacent tissue when the balloon catheter apparatus and associated system 10 is targeting tissue at a radial depth of 2.0 mm to 4.0 mm from the inner surface of an arterial wall while the various cooling and heat transfer mechanisms described herein are not employed. FIG. 23 depicts an example of the effect the balloon catheter apparatus and associated system 10 may have on adjacent tissue when the balloon catheter apparatus and associated system 10 is targeting tissue at a radial depth of 2.0 mm to 4.0 mm from the inner surface of an arterial wall while the various cooling and heat transfer mechanisms described herein are employed. As demonstrated by FIGS. 21 and 23, the use of the various cooling and heat transfer mechanisms described herein result in less thermal damage to the arterial wall and, instead, enable the balloon catheter apparatus and associated system 10 to focus the thermal heat generated by the microwave emission on the targeted tissues. One skilled in the art will appreciate that one set of operational variables, e.g., frequency selection, pulse duration, time of treatment, emitter design, etc., will not result in a consistent or uniform temperature gradient map for every patient. Numerous variables, including, but not limited to, patient anatomy, bioimpedance, and the type of targeted tissue, needs to be taken into account when selecting the proper variables to operate the balloon catheter apparatus and associated system. Additional tissue temperature gradients are contemplated to achieve the desired ablation as described herein, and FIG. 20-23 are presented solely as examples and are not meant to suggest that the balloon catheter apparatus and associated system 10 is incapable of alternate tissue temperature gradients that can accomplish the desired ablation of targeted tissue and achieve the associated therapeutic benefit.

Figure 25A:
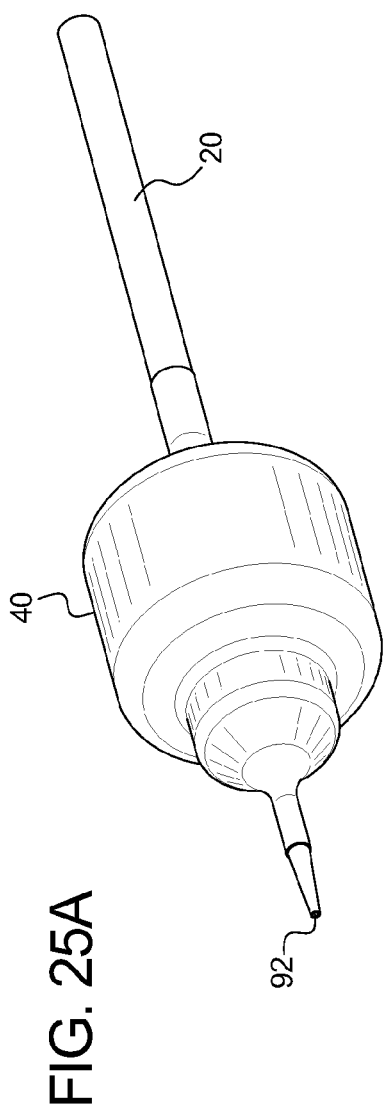
FIGS. 25A, 25B, and 25C illustrate another embodiment of a non-symmetrical inflatable balloon of the balloon catheter apparatus.
Figure 25B:
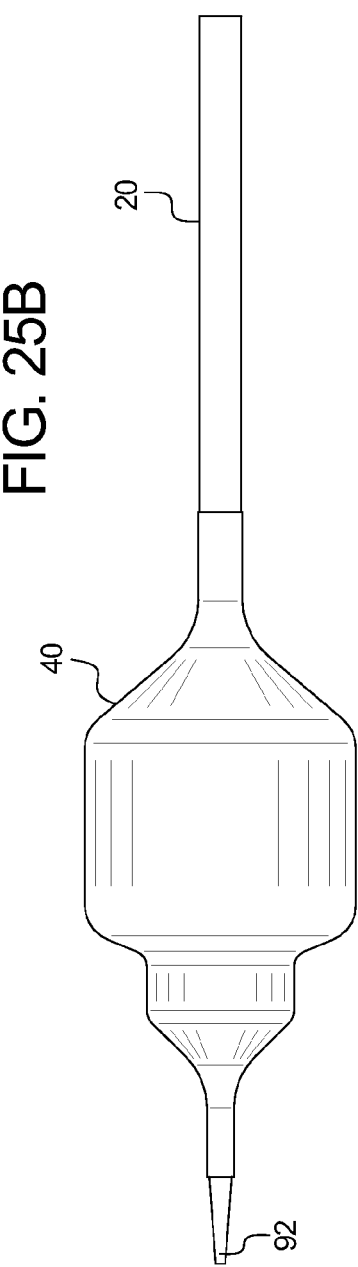
Figure 25C:
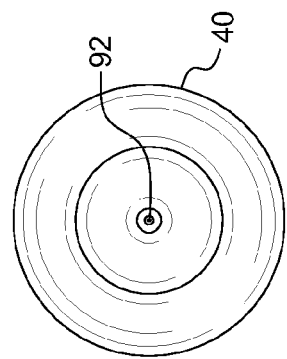

FIGS. 24-26 depict various embodiments of the inflatable balloon 40 of the balloon catheter apparatus. Particularly, FIGS. 24-26 show non-symmetrical balloon geometries that are apparent when the balloon 40 is inflated. FIGS. 24A, 24B, and 24C are perspective, side, and end views, respectively, of a non-symmetrical inflatable balloon 40 when inflated. As shown in FIG. 24C, the inflatable balloon 40 is non-symmetrical with respect to the longitudinal axis. FIGS. 25A, 25B, and 25C are perspective, side, and end views, respectively, of another non-symmetrical inflatable balloon 40 when inflated. As shown in FIG. 25C, the inflatable balloon 40 is symmetrical with respect to the longitudinal axis, but as shown in FIG. 25B, the inflatable balloon 40 varies in profile lengthwise along the longitudinal axis. FIGS. 26A, 26B, and 26C depict a tapered balloon geometry of another embodiment of inflatable balloon 40 when inflated. As shown in FIG. 26C, the inflatable balloon 40 is symmetrical with respect to the longitudinal axis, but as shown in FIG. 26B, the inflatable balloon 40 varies in profile lengthwise along the longitudinal axis.

Figure 27:
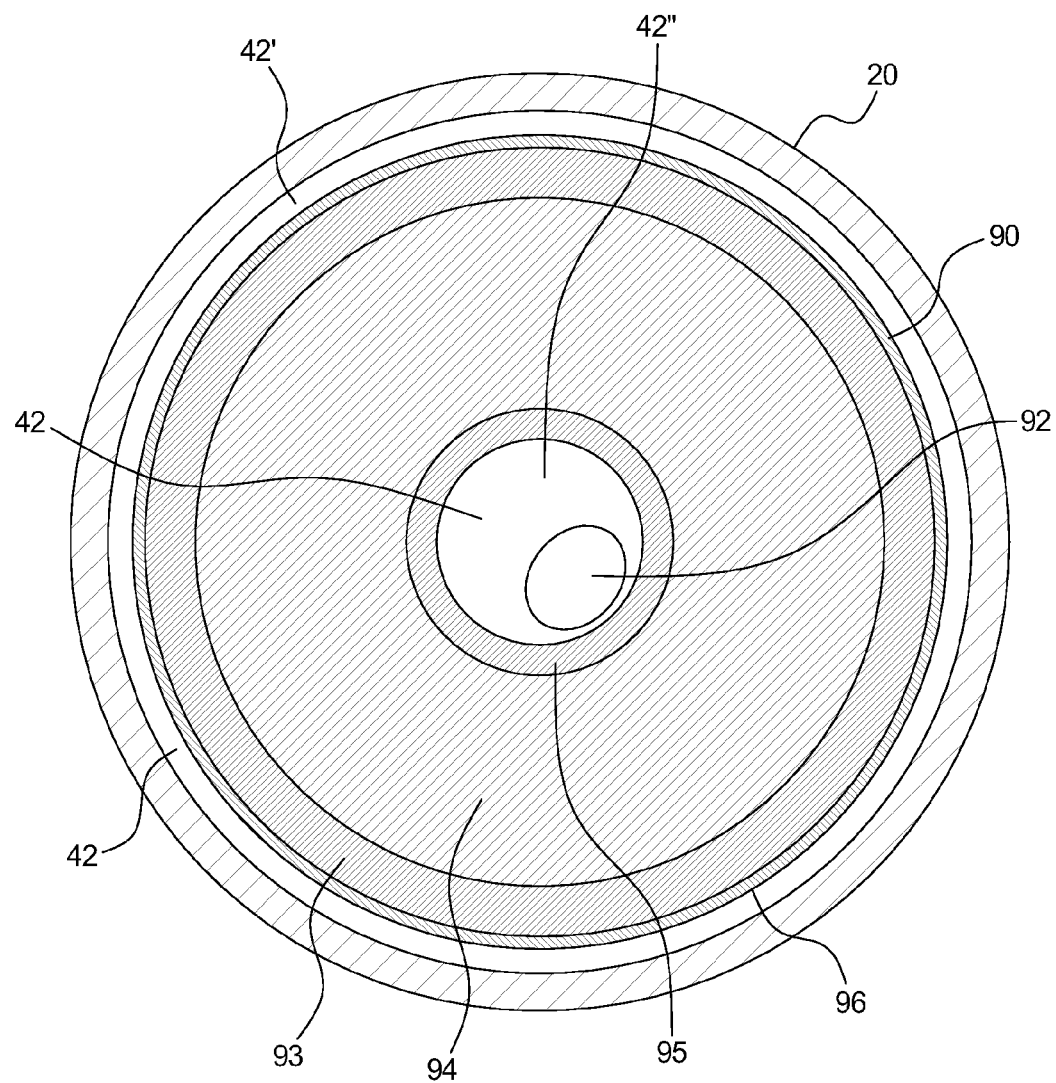
FIG. 27 illustrates a cross section of an embodiment of the inflatable balloon catheter apparatus along the catheter shaft.

FIG. 27 depicts one embodiment of a cross-section of the catheter 20 shaft proximal to the inflatable balloon 40. In this embodiment, a coolant channel 42 is located within a cable 90. The guide wire 92 may be housed within a central lumen that may function as a coolant channel 42. In this embodiment, the central lumen serves as both a coolant channel 42 and a guide wire 92 lumen, the latter to permit advancement of the balloon within the patient's vasculature. The inner conductor 95 of the cable 90 forms the boundaries of the central lumen. A dielectric material 94 surrounds the inner conductor. The dielectric material 94 comprises a dielectric material found in coaxial cables, which is known by those of ordinary skill in the art. The dielectric material 94 differs from the dielectric agents described above that traverse through one or more coolant channels 42. Surrounding the dielectric material 94 is an outer conductor 93. A cable outer jacket 96 surrounds the outer conductor 93. The area or annulus between the cable 90 and the catheter 20 forms another coolant channel 42'. In this embodiment, a dielectric agent would be introduced from a port into the balloon catheter apparatus. The port would carry the dielectric agent into coolant channel 41". The dielectric agent would flow through the coolant channel 42" into the balloon. A return aperture or apertures would be located at some location distal to the cross-section depicted in FIG. 27. The one or more return apertures would allow the dielectric agent to inflate the balloon and be circulated towards the proximal end of the balloon catheter apparatus. One or more return apertures may be connected to coolant channels 42' to return the dielectric agent to the proximal end of the balloon catheter apparatus in order for the dielectric agent to be cooled or disposed. In other embodiments, the dielectric agent may exit the distal end of the balloon through one or more irrigation ports described above.

Figure 28:
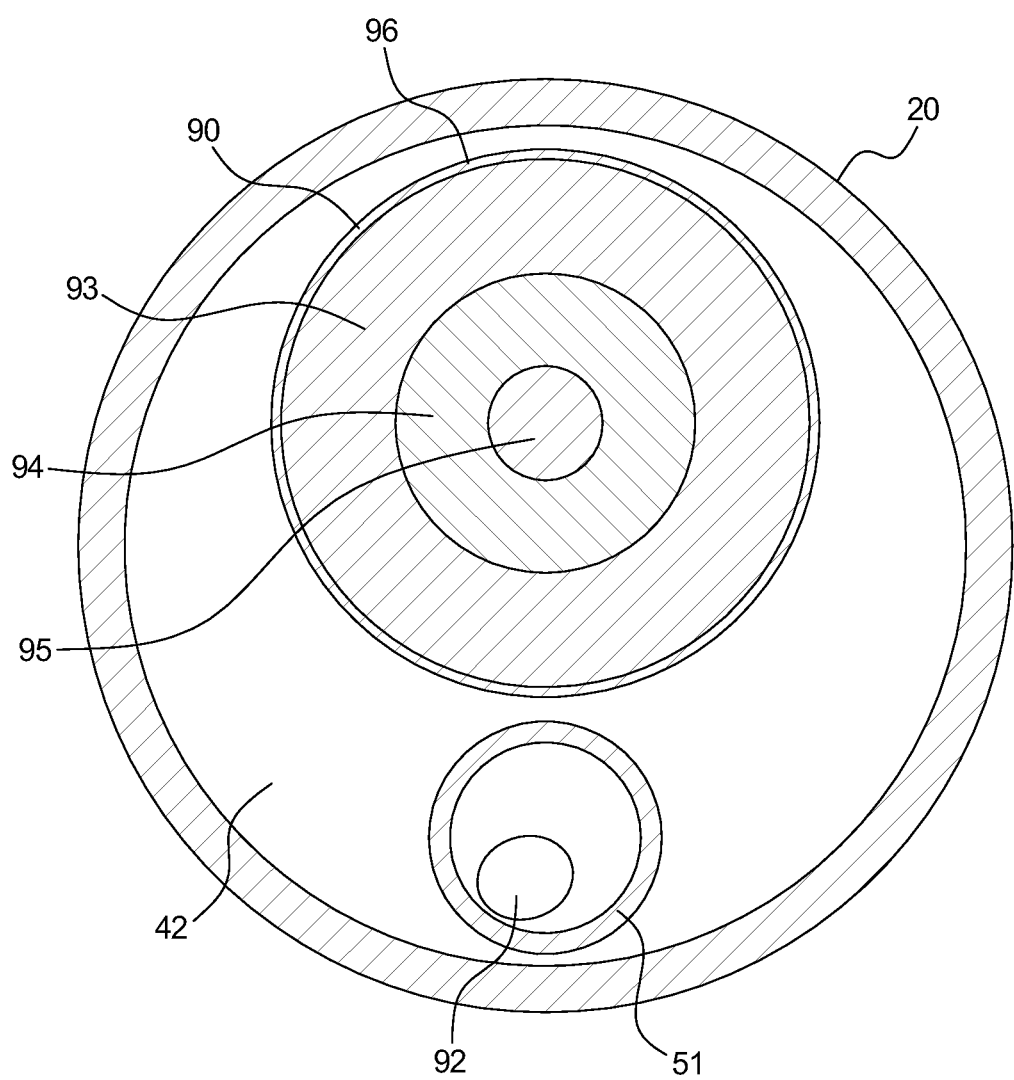
FIG. 28 illustrates a cross section of another embodiment of the inflatable balloon catheter apparatus along the catheter shaft.

FIG. 28 depicts one embodiment of a cross-section of the catheter 20 shaft proximal to the inflatable balloon 40. In this embodiment, a coaxial cable 90 is located within the catheter 20 shaft. The coaxial cable comprises an inner conductor 95, a dielectric material 94 (as described in FIG. 27), an outer conductor 93, and a cable outer jacket 96. A guide wire lumen 51 houses a guide wire 92. The space in the catheter 20 not occupied by the cable 90 or the guide wire lumen 51 forms a coolant channel 42.

While specific embodiments have been described in detail, it will be appreciated by those skilled in the art that various modifications and alternatives to those details could be developed in light of the overall teachings of the disclosure. In particular, the balloon catheter apparatus and associated system described herein may be used in any number of different ways and in different applications not necessarily involving procedures for treating cardiovascular hypertension. Accordingly, the disclosure herein is meant to be illustrative only and not limiting as to its scope and should be given the full breadth of the appended claims and any equivalents thereof.

What is claimed is:

1. A microwave ablation system for use in renal denervation to treat pulmonary hypertension, comprising:
   a balloon catheter apparatus, comprising
      a catheter configured to house a coaxial cable and at least two coolant channels;
      an inflatable balloon located at the distal end of the catheter, the inflatable balloon comprising a length of 10 to 45 millimeters; and
      an antenna positioned in the inflatable balloon and in communication with the coaxial cable, the antenna configured to emit microwave energy to a target tissue zone located greater than 5.0 millimeters and less than 12.0 millimeters radially from an inner wall of an artery, wherein tissue within the target tissue zone is heated by the emitted microwave energy to a temperature from 40° C. to 100° C., and wherein the antenna is selected from the group of antennas consisting of a slot antenna, a multi-slot antenna, and a choked slot antenna;
      wherein the at least two coolant channels are configured to cool one or more elements of the microwave ablation system and/or non-targeted tissue lying outside the target tissue zone that may be heated as a consequence of emitting microwave energy from the antenna, and wherein (1) the at least two coolant channels form a circulation loop to continuously cool the balloon catheter apparatus and the non-targeted tissue, and (2) the at least two coolant channels are adapted to convey a fluid selected from the group consisting of saline, carbon dioxide, and Ringer's solution, and (2); and
   a control system comprising
      a fluid pump configured to introduce fluid into a proximal end of the catheter;
      a power amplifier capable of generating microwave energy for delivery to the target tissue zone for at least one energy application cycle ranging from 60 seconds to 600 seconds at a frequency ranging from 2.4 GHz to 2.5 GHz; and
      a computer system configured to monitor and/or regulate the delivery of microwave energy to the target tissue, the fluid pump, at least one sensor, and antenna reflected power, wherein the computer system comprises a safety algorithm to ensure the microwave ablation system operates within acceptable temperature and power ranges.

2. The microwave ablation system of claim 1, wherein the target tissue zone is heated by the emitted microwave energy to a temperature ranging from 48° C. to 75° C.

3. The microwave ablation system of claim 1, wherein the inflatable balloon when inflated comprises a tapered geometry.

4. The microwave ablation system of claim 1, wherein the inflatable balloon when inflated comprises a non-symmetric geometry.

5. The microwave ablation system of claim 1, wherein the at least one application cycle contains more than one pulse of microwave energy.

6. The microwave ablation system of claim 1, wherein the computer system is configured to monitor a pressure of fluid in the one or more coolant channels and adjust a flow rate and/or fluid volume output of the fluid pump.

7. The microwave ablation system of claim 1, wherein the one or more coolant channels is in communication with an irrigation port configured to deliver fluid to the patient's vasculature after the fluid has cooled elements of the balloon catheter apparatus and/or non-targeted tissue.

8. The microwave ablation system of claim 1, wherein the catheter includes a lumen positioned adjacent the coaxial cable, wherein the lumen is configured to receive a guide wire.

9. The microwave ablation system of claim 1, wherein the coaxial cable comprises a central lumen configured to receive a guide wire and to transport fluid to the balloon.

10. The microwave ablation system of claim 1, wherein one of the one or more coolant channels is located inside the coaxial cable.

11. The microwave ablation system of claim 1, wherein a distal portion of the catheter is more flexible than a proximal portion of the catheter.

12. The microwave ablation system of claim 1, wherein a distal portion of the coaxial cable is more flexible than a proximal portion of the coaxial cable.

13. The microwave ablation system of claim 1, wherein the catheter includes one or more sensors connected to one or more sensor cables and the one or more sensor cables are in communication with the control system.

14. The microwave ablation system of claim 1, wherein the catheter includes a radiometer.

15. The microwave ablation system of claim 1, wherein the antenna is configured to receive reflected radiation information from the target tissue zone, and transmit the radiation information to the control system via the coaxial cable.

16. The microwave ablation system of claim 1, wherein the control system is capable of phase shifting the emitted microwave energy.

17. The microwave ablation system of claim 1, wherein the control system is capable of frequency sweeping the emitted microwave energy.

18. The microwave ablation system of claim 1, wherein the control system is configured to permit selection of a predetermined dose amount of microwave energy from among a plurality of predetermined dose amounts of microwave energy to be emitted by the antenna.

* * * * *